(12) United States Patent
Bamberg et al.

(10) Patent No.: US 7,741,326 B2
(45) Date of Patent: Jun. 22, 2010

(54) INDOLE AND BENZOFURAN 2-CARBOXAMIDE DERIVATIVES AND USES THEREOF

(75) Inventors: Joe Timothy Bamberg, East Palo Alto, CA (US); Counde O'Yang, Sunnyvale, CA (US); Meng Sui, Sunnyvale, CA (US); Shu-Hai Zhao, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 112 days.

(21) Appl. No.: 11/983,319

(22) Filed: Nov. 8, 2007

(65) Prior Publication Data

US 2008/0146587 A1 Jun. 19, 2008

Related U.S. Application Data

(60) Provisional application No. 60/858,030, filed on Nov. 9, 2006.

(51) Int. Cl.
*A61K 31/404* (2006.01)
*C07D 209/42* (2006.01)
*A61K 31/4524* (2006.01)
*A61K 31/454* (2006.01)
*C07D 401/04* (2006.01)
*C07D 405/04* (2006.01)

(52) U.S. Cl. .................. 514/254.09; 544/373; 544/379; 546/213; 546/214; 514/320; 514/323

(58) Field of Classification Search ........................ None
See application file for complete search history.

(56) References Cited

U.S. PATENT DOCUMENTS

| | | | |
|---|---|---|---|
| 5,272,145 A | 12/1993 | Prasit et al. | |
| 5,273,980 A | 12/1993 | Frenette et al. | |
| 5,290,798 A | 3/1994 | Gillard et al. | |
| 5,308,850 A | 5/1994 | Gillard et al. | |
| 6,255,306 B1 * | 7/2001 | Macor .................. | 514/253.09 |
| 6,391,882 B1 | 5/2002 | Moltzen et al. | |
| 2003/0045527 A1 | 3/2003 | Briggs et al. | |
| 2003/0073700 A1 | 4/2003 | Beard et al. | |
| 2003/0195244 A1 | 10/2003 | Hsieh et al. | |
| 2004/0063724 A1 | 4/2004 | Madera et al. | |
| 2004/0072844 A1 | 4/2004 | Madera et al. | |

FOREIGN PATENT DOCUMENTS

| | | |
|---|---|---|
| CA | 2 060 557 | 6/2002 |
| EP | 0 146 243 A1 | 6/1985 |
| EP | 0 396 124 A2 | 7/1990 |
| EP | 0 396 124 A3 | 7/1990 |
| EP | 0 535 923 A1 | 7/1993 |
| EP | 0 535 924 A1 | 7/1993 |
| EP | 0 535 926 A1 | 7/1993 |
| EP | 0 419 049 B1 | 4/1995 |
| EP | 0 535 925 B1 | 4/1996 |
| WO | WO 93/16069 A1 | 8/1993 |
| WO | WO 93/20078 A1 | 10/1993 |
| WO | WO 93/25546 A1 | 12/1993 |
| WO | WO 96/03400 A1 | 2/1996 |
| WO | WO 96/41802 A1 | 12/1996 |
| WO | WO 98/08818 A1 | 3/1998 |
| WO | WO 99/33800 A1 | 7/1999 |
| WO | WO 99/55672 A2 | 11/1999 |
| WO | WO 99/55672 A3 | 11/1999 |
| WO | WO 99/67237 A1 | 12/1999 |
| WO | WO 02/46178 A2 | 6/2002 |
| WO | WO 02/46178 A3 | 6/2002 |
| WO | WO 02/098857 A1 | 12/2002 |
| WO | WO 02/102774 A1 | 12/2002 |
| WO | WO 03/004485 A1 | 1/2003 |
| WO | WO 03/022214 A2 | 3/2003 |
| WO | WO 03/022214 A3 | 3/2003 |
| WO | WO 03/029212 A1 | 4/2003 |

* cited by examiner

*Primary Examiner*—Emily Bernhardt
(74) *Attorney, Agent, or Firm*—Robert C. Hall

(57) ABSTRACT

Compounds of formula I or formula II:

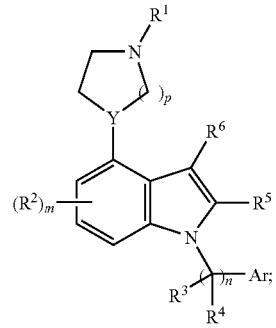

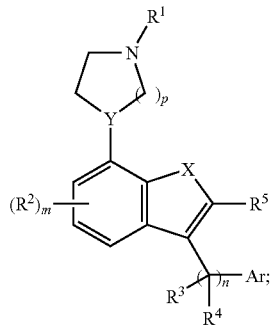

or pharmaceutically acceptable salts thereof, wherein m, n, p, Ar $R^1$, $R^2$, $R^4$, and $R^5$ are as defined herein. The invention also provides methods for preparing, compositions comprising, and methods for using compounds.

5 Claims, No Drawings

INDOLE AND BENZOFURAN 2-CARBOXAMIDE DERIVATIVES AND USES THEREOF

CROSS REFERENCE TO RELATED APPLICATIONS

This application claims the benefit of priority of U.S. Provisional Patent Application Ser. No. 60/858,030 filed Nov. 9, 2006, the disclosure of which is incorporated herein by reference in its entirety.

FIELD OF THE INVENTION

This invention relates to substituted indole and benzofuran compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of formula I or formula II:

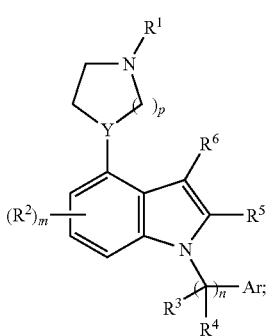

I

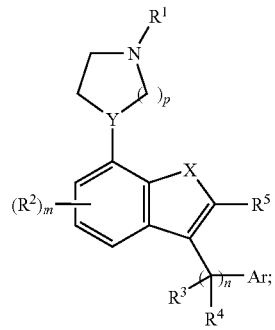

II or pharmaceutically acceptable salts thereof, wherein:
  m is from 0 to 3;
  n is 1 or 2;
  p is 1 or 2;
  X is:
  —O—;
  —S—; or
  —NR$^7$—;
  Y is N or CH when p is 2, and Y is CH when p is 1.
  Ar is:
  optionally substituted aryl; or
  optionally substituted heteroaryl;
  R$^1$ is:
  hydrogen; or
  C$_{1-6}$alkyl;
  each R$^2$ is independently:
  halo;
  C$_{1-6}$alkyl;
  halo-C$_{1-6}$alkyl;
  halo-C$_{1-6}$alkoxy;
  C$_{1-6}$alkoxy;
  hydroxy;
  hetero-C$_{1-6}$alkyl;
  cyano;
  nitro;
  amino;
  —(CH$_2$)$_q$—S(O)$_r$—R$^a$;
  —(CH$_2$)$_q$—C(=O)—NR$^b$R$^c$;
  —(CH$_2$)$_q$—SO$_2$—NR$^b$R$^c$;
  —CH$_2$)$_q$—N(R$^j$)—C(=O)—R$^d$, or
  —(CH$_2$)$_q$—C(=O)—R$^d$;
  wherein;
    q is 0 or 1;
    r is from 0 to 2; and
    R$^a$, R$^b$ and R$^c$ each independently is hydrogen or C$_{1-6}$alkyl, and R$^d$ is hydrogen, C$_{1-6}$alkyl, C$_{1-6}$alkoxy or hydroxy;
  R$^3$ and R$^4$ each independently is hydrogen or C$_{1-6}$alkyl;
  R$^5$ is:
  nitrile
  —C(O)—NR$^e$R$^f$;
  —C(O)—R$^g$; or
  —SO$_2$—R$^g$;
  wherein R$^e$ and R$^f$ each independently is hydrogen or C$_{1-6}$alkyl, and R$^g$ is C$_{1-6}$alkyl;
  R$^6$ is:
  hydrogen;
  halo;

$C_{1-6}$alkyl;
halo-$C_{1-6}$alkyl;
halo-$C_{1-6}$alkoxy;
$C_{1-6}$alkoxy;
hetero-$C_{1-6}$alkyl; or
cyano; and
$R^7$ is:
hydrogen;
$C_{1-6}$alkyl; or
hetero-$C_{1-6}$alkyl.

The invention further provides compositions comprising, methods for preparing and methods for using the aforementioned compounds.

DETAILED DESCRIPTION OF THE INVENTION

The invention provides substituted indole compounds, associated compositions, methods for use as therapeutic agents, and methods of preparation thereof.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. Preferred aryl are phenyl and naphthyl, and more preferably phenyl, which may be optionally substituted as defined herein.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. Preferred heteroaryl include pyridinyl, pyrimidinyl, thiophenyl, quinolinyl and indolyl, which may be optionally substituted as defined herein.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl. Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen, nitrogen or sulfur atom in the structures herein indicates the presence of a hydrogen.

Compounds of the Invention

The invention provides compounds of the formula I or II:

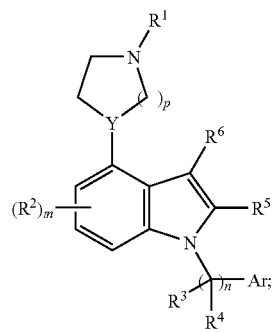

I

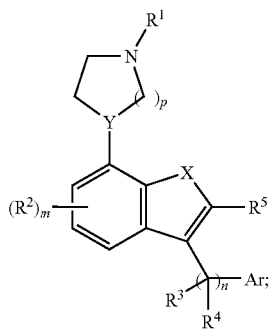

II or a pharmaceutically acceptable salt thereof, wherein:
m is from 0 to 3;
n is 1 or 2;
p is 1 or 2;
X is:
—O—;
—S—; or
—$NR^7$—;
Y is N or CH when p is 2, and Y is CH when p is 1.
Ar is:
optionally substituted aryl; or
optionally substituted heteroaryl;
$R^1$ is:
hydrogen; or
$C_{1-6}$alkyl;
each $R^2$ is independently:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
nitro;
amino;
—$(CH_2)_q$—S(O)$_r$—$R^a$;
—$(CH_2)_q$—C(=O)—$NR^bR^c$;
—$(CH_2)_q$—$SO_2$—$NR^bR^c$;
—$(CH_2)_q$—N($R^j$)—C(=O)—$R^d$, or
—$(CH_2)_q$—C(=O)—$R^d$;

wherein;
q is 0 or 1;
r is from 0 to 2; and
$R^a$, $R^b$ and $R^c$ each independently is hydrogen or $C_{1-6}$alkyl, and $R^d$ is hydrogen, $C_{1-6}$alkyl, $C_{1-6}$alkoxy or hydroxy;
$R^3$ and $R^4$ each independently is hydrogen or $C_{1-6}$alkyl;
$R^5$ is:
nitrile
—C(O)—$NR^eR^f$;
—C(O)—$R^g$; or
—$SO_2$—$R^g$;
wherein $R^e$ and $R^f$ each independently is hydrogen or $C_{1-6}$alkyl, and $R^g$ is $C_{1-6}$alkyl;
$R^6$ is:
hydrogen;
halo;
$C_{1-6}$alkyl;
halo-$C_{1-6}$alkyl;
halo-$C_{1-6}$alkoxy;
$C_{1-6}$alkoxy;
hetero-$C_{1-6}$alkyl; or
cyano; and
$R^7$ is:
hydrogen;
$C_{1-6}$alkyl; or
hetero-$C_{1-6}$alkyl.

In certain embodiments of formula I or formula II, n is 1.
In certain embodiments of formula I or formula II, p is 1.
In certain embodiments of formula I or formula II, p is 0.
In certain embodiments of formula I or formula II, $R^3$ and $R^4$ are hydrogen.
In certain embodiments of formula I or formula II, $R^5$ is —C(O)—$NR^eR^f$.
In certain embodiments of formula I or formula II, $R^5$ is —C(O)—$R^g$.
In certain embodiments of formula I or formula II, $R^5$ is —$SO_2$—$R^g$.
In certain embodiments of formula I or formula II, Ar is optionally substituted aryl.
In certain embodiments of formula I or formula II, Ar is optionally substituted phenyl.
In certain embodiments of formula I or formula II, Ar is optionally substituted heteroaryl.
In certain embodiments of formula I, Ar is phenyl or naphthyl optionally substituted once or twice with any of halo, $C_{1-6}$alkyl, halo-$C_{1-6}$alkyl, halo-$C_{1-6}$alkoxy, $C_{1-6}$alkoxy, hydroxy, hetero-$C_{1-6}$alkyl, cyano, nitro, amino, —C(O)—$NR^eR^f$; —C(O)—$R^g$; or —$SO_2$—$R^g$ wherein $R^e$, $R^f$ and $R^g$ are hydrogen or $C_{1-6}$alkyl.
In certain embodiments of formula I, Ar is phenyl optionally substituted once or twice with any of halo, $C_{1-6}$alkyl, halo-$C_{1-6}$alkyl, halo-$C_{1-6}$alkoxy, $C_{1-6}$alkoxy, hydroxy, hetero-$C_{1-6}$alkyl, cyano, nitro, amino, —C(O)—$NR^eR^f$; —C(O)—$R^g$; or —$SO_2$—$R^g$ wherein $R^e$, $R^f$ and $R^g$ are hydrogen or $C_{1-6}$alkyl.
In certain embodiments of formula I, Ar is phenyl optionally substituted once or twice with any of halo, $C_{1-6}$alkyl, halo-$C_{1-6}$alkyl, $C_{1-6}$alkoxy, hydroxy or cyano.
In certain embodiments of formula I, Ar is heteroaryl optionally substituted once or twice with any of halo, $C_{1-6}$alkyl, halo-$C_{1-6}$alkyl, halo-$C_{1-6}$alkoxy, $C_{1-6}$alkoxy, hydroxy, hetero-$C_{1-6}$alkyl, cyano, nitro, amino, —C(O)—$NR^eR^f$; —C(O)—$R^g$; or —$SO_2$—$R^g$ wherein $R^e$, $R^f$ and $R^g$ are hydrogen or $C_{1-6}$alkyl.

In certain embodiments of formula I, Ar is heteroaryl optionally substituted once or twice with any of halo, $C_{1-6}$alkyl, halo-$C_{1-6}$alkyl, $C_{1-6}$alkoxy, hydroxy or cyano.
In certain embodiments of formula I or formula II, m is 0 or 1.
In certain embodiments of formula I or formula II, $R^e$ and $R^f$ each independently is hydrogen or methyl.
In certain embodiments of formula I or formula II, $R^6$ is hydrogen.
In certain embodiments of formula I or formula II, $R^6$ is hydrogen or methyl.
In certain embodiments of formula I or formula II, Y is N.
In certain embodiments of formula I or formula II, Y is CH.
In certain embodiments of formula I or formula II, p is 2 and Y is N.
In certain embodiments of formula I or formula II, p is 2 and Y is CH.
In certain embodiments of formula I or formula II, $R^2$ is halo, $C_{1-6}$alkyl, halo-$C_{1-6}$alkyl, halo-$C_{1-6}$alkoxy, $C_{1-6}$alkoxy or cyano.
In certain embodiments of formula I or formula II, $R^2$ is halo or $C_{1-6}$alkyl.
In certain embodiments of formula I or formula II, Ar is phenyl optionally substituted once or twice with any of halo, $C_{1-6}$alkyl, halo-$C_{1-6}$alkyl, halo-$C_{1-6}$alkoxy, $C_{1-6}$alkoxy or cyano.
In certain embodiments of formula II, X is —O—.
In certain embodiments of formula II, X is —$NR^7$.
In certain embodiments of formula II, X is —S—.
In certain embodiments of formula II, X is —NH—.
In certain embodiments of the invention, the subject compounds are of formula III or IV:

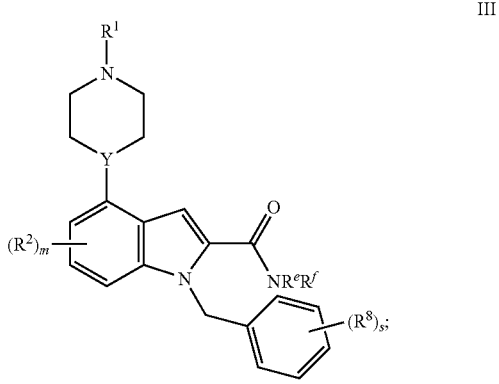

III

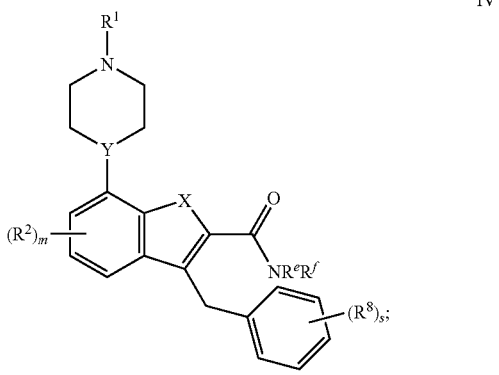

IV wherein:
s is from 1 to 4;
each $R^8$ is independently:
halo;
$C_{1-6}$alkyl;
halo-$C_{1-6}$alkyl;
halo-$C_{1-6}$alkoxy;
$C_{1-6}$alkoxy;
hetero-$C_{1-6}$alkyl;
cyano;
nitro;
amino;
—$(CH_2)_q$—S(O)$_r$—$R^a$;
—$(CH_2)_q$—C(=O)—$NR^bR^c$;
—$(CH_2)_q$—$SO_2$—$NR^bR^c$;
—$(CH_2)_q$—$N(R^f)$—C(=O)—$R^d$, or
—$(CH_2)_q$—C(=O)—$R^d$;
m, q, r, X, Y, $R^1$, $R^2$, $R^a$, $R^b$, $R^c$, $R^d$, $R^e$ and $R^f$ are as defined herein.

In certain embodiments of formula III or formula IV, m is 0 or 1.

In certain embodiments of formula III or formula IV, $R^e$ and $R^f$ each independently is hydrogen or methyl.

In certain embodiments of formula III or formula IV, $R^1$ is hydrogen or methyl.

In certain embodiments of formula III or formula IV, Y is N.

In certain embodiments of formula III or formula IV, Y is CH.

In certain embodiments of formula III or formula IV, $R^2$ is halo, $C_{1-6}$alkyl, halo-$C_{1-6}$alkyl, halo-$C_{1-6}$alkoxy, $C_{1-6}$alkoxy or cyano.

In certain embodiments of formula III or formula IV, $R^2$ is halo or $C_{1-6}$ alkyl.

In certain embodiments of formula III or formula IV, s is 0, 1 or 2.

In certain embodiments of formula III or formula IV, s is 0 or 1.

In certain embodiments of formula III or formula IV, $R^8$ is halo, $C_{1-6}$alkyl, halo-$C_{1-6}$alkyl, halo-$C_{1-6}$alkoxy, $C_{1-6}$alkoxy or cyano.

In certain embodiments of formula III or formula IV, $R^8$ is halo.

In certain embodiments of formula IV, X is —O—.

In certain embodiments of formula IV, X is —$NR^7$.

In certain embodiments of formula IV, X is —S—.

In certain embodiments of formula IV, X is —NH—.

In embodiments of the invention where any of $R^1$, $R^2$, $R^3$, $R^4$, $R^5$, $R^6$, $R^7$, $R^8$, $R^9$, $R^{10}$, $R^a$, $R^b$, $R^c$ and $R^d$ are alkyl or an alkyl moiety, such alkyl is preferably are lower alkyl, i.e. $C_1$-$C_6$alkyl, and more preferably $C_1$-$C_4$alkyl. In embodiments where Y is S, A is preferably —$NR^3$—.

It should be understood that the scope of this invention encompasses not only the various isomers which may exist but also the various mixture of isomers which may be formed. Furthermore, the scope of the present invention also encompasses solvates and salts of compounds of formula I.

Representative compounds in accordance with the invention are shown in Table 1 together with melting point (HCl or trifluoroacetic acid (TFA) salts) or mass spectrum M+H, and the experimental examples (described below) associated with each compound.

TABLE 1

| # | Structure | Name (Autonom ™) | MP ° C./M + H |
|---|---|---|---|
| 1 | 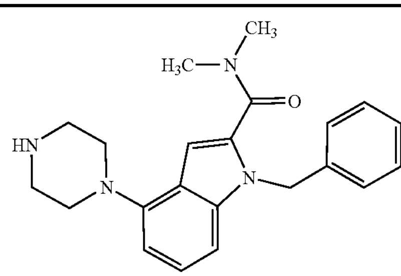 | 1-Benzyl-4-piperazin-1-yl-1H-indole-2-carboxylic acid dimethylamide | 363 |
| 2 | 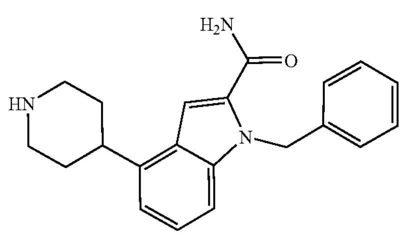 | 1-Benzyl-4-piperidin-4-yl-1H-indole-2-carboxylic acid amide | 334 |
| 3 | 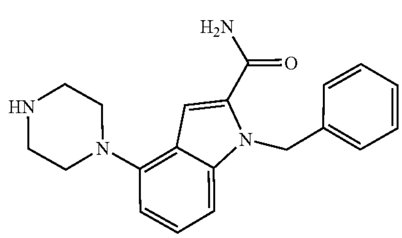 | 1-Benzyl-4-piperazin-1-yl-1H-indole-2-carboxylic acid amide | >300 (HCl salt) |

TABLE 1-continued

| # | Structure | Name (Autonom ™) | MP ° C./M + H |
|---|---|---|---|
| 4 | 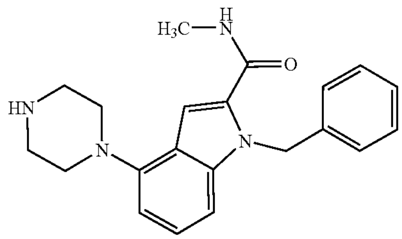 | 1-Benzyl-4-piperazin-1-yl-1H-indole-2-carboxylic acid methylamide | 349 |
| 5 | 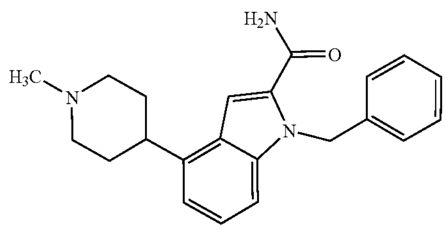 | 1-Benzyl-4-(1-methyl-piperidin-4-yl)-1H-indole-2-carboxylic acid amide | 348 |
| 6 | 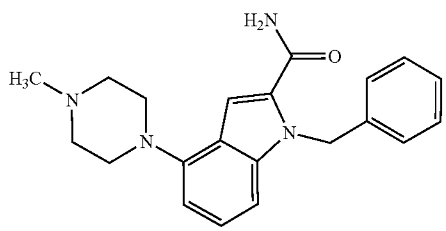 | 1-Benzyl-4-(4-methyl-piperazin-1-yl)-1H-indole-2-carboxylic acid amide | 292.5-294.3 (HCl Salt) |
| 7 | 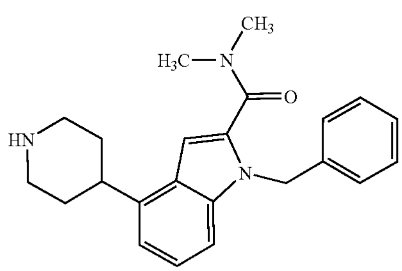 | 1-Benzyl-4-piperidin-4-yl-1H-indole-2-carboxylic acid dimethylamide | 362 |
| 8 | 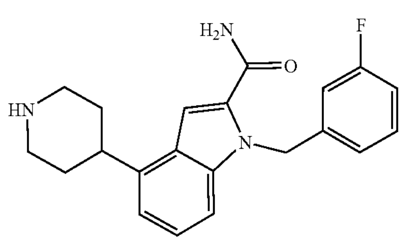 | 1-(3-Fluoro-benzyl)-4-piperidin-4-yl-1H-indole-2-carboxylic acid amide | >300 (HCl salt) |
| 9 | 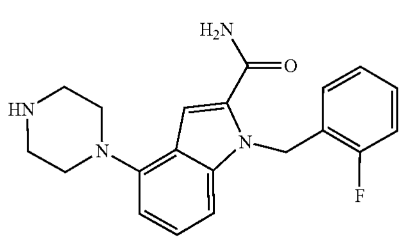 | 1-(2-Fluoro-benzyl)-4-piperazin-1-yl-1H-indole-2-carboxylic acid amide | >300 (HCl salt) |

TABLE 1-continued

| # | Structure | Name (Autonom ™) | MP ° C./M + H |
|---|---|---|---|
| 10 | 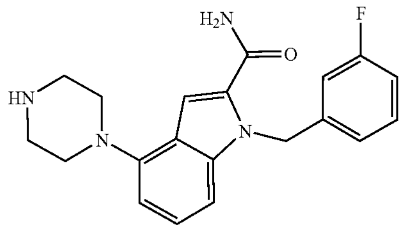 | 1-(3-Fluoro-benzyl)-4-piperazin-1-yl-1H-indole-2-carboxylic acid amide | >300 (HCl salt) |
| 11 | 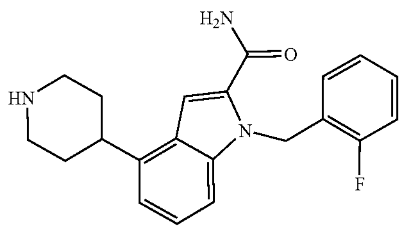 | 1-(2-Fluoro-benzyl)-4-pipendin-4-yl-1H-indole-2-carboxylic acid amide | 352 |
| 12 | 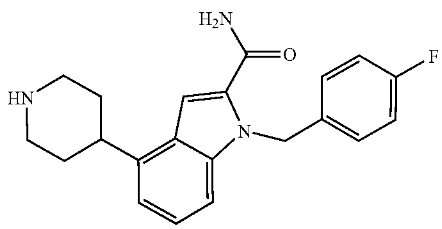 | 1-(4-Fluoro-benzyl)-4-piperidin-4-yl-1H-indole-2-carboxylic acid amide | >300 (HCl salt) |
| 13 | 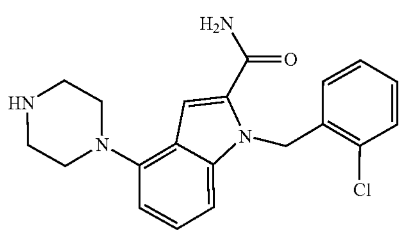 | 1-(2-Chloro-benzyl)-4-piperazin-1-yl-1H-indole-2-carboxylic acid amide | >300 (HCl salt) |
| 14 | 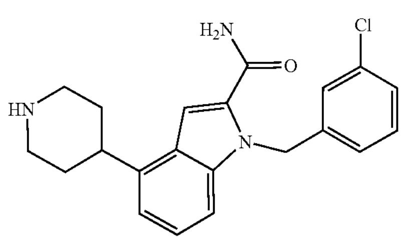 | 1-(3-Chloro-benzyl)-4-piperazin-1-yl-1H-indole-2-carboxylic acid amide | >300 (HCl salt) |
| 15 | 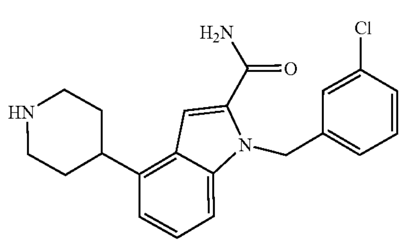 | 1-(3-Chloro-benzyl)-4-piperidin-4-yl-1H-indole-2-carboxylic acid amide | >300 (HCl salt) |

TABLE 1-continued

| # | Structure | Name (Autonom ™) | MP ° C./M + H |
|---|---|---|---|
| 16 | 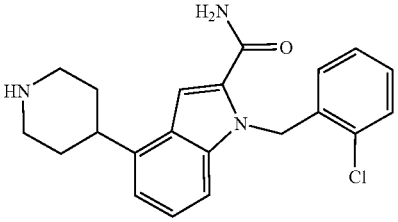 | 1-(2-Chloro-benzyl)-4-piperidin-4-yl-1H-indole-2-carboxylic acid amide | >300 (HCl salt) |
| 17 | 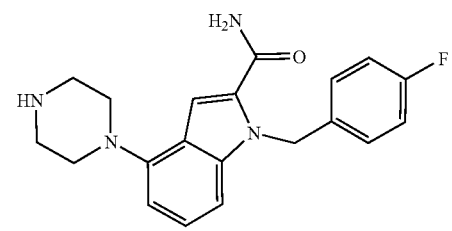 | 1-(4-Fluoro-benzyl)-4-piperazin-1-yl-1H-indole-2-carboxylic acid amide | 353 |
| 18 | 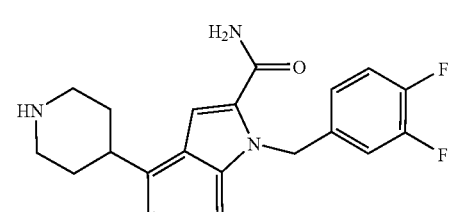 | 1-(3,4-Difluoro-benzyl)-4-piperidin-4-yl-1H-indole-2-carboxylic acid amide | 370 |
| 19 | 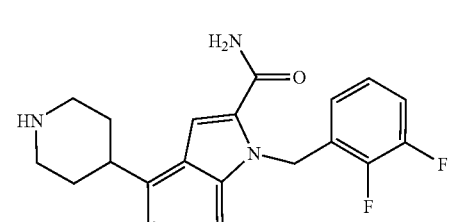 | 1-(2,3-Difluoro-benzyl)-4-piperidin-4-yl-1H-indole-2-carboxylic acid amide | >300 (HCl salt) |
| 20 | 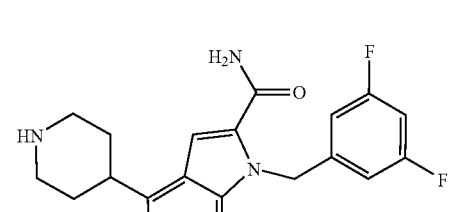 | 1-(3,5-Difluoro-benzyl)-4-piperidin-4-yl-1H-indole-2-carboxylic acid amide | 370 |
| 21 | 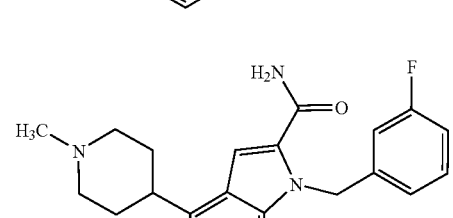 | 1-(3-Fluoro-benzyl)-4-(1-methyl-piperidin-4-yl)-1H-indole-2-carboxylic acid amide | 366 |

TABLE 1-continued

| # | Structure | Name (Autonom ™) | MP ° C./M + H |
|---|---|---|---|
| 22 | 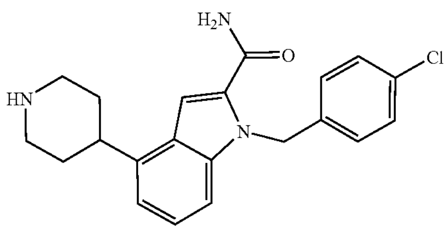 | 1-(4-Chloro-benzyl)-4-piperidin-4-yl-1H-indole-2-carboxylic acid amide | 368 |
| 23 | 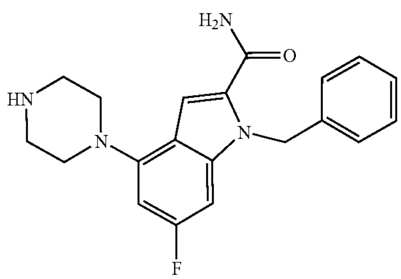 | 1-Benzyl-6-fluoro-4-piperazin-1-yl-1H-indole-2-carboxylic acid amide | >300 (HCl salt) |
| 24 | 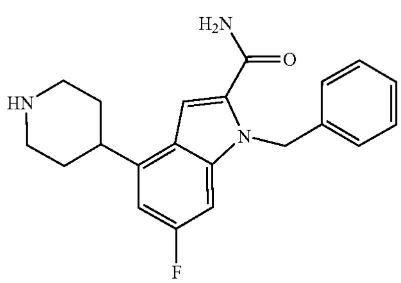 | 1-Benzyl-6-fluoro-4-piperidin-4-yl-1H-indole-2-carboxylic acid amide | 352 |
| 25 | 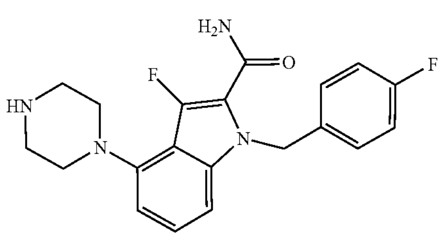 | 3-Fluoro-1-(4-fluoro-benzyl)-4-piperazin-1-yl-1H-indole-2-carboxylic acid amide | 371 |
| 26 | 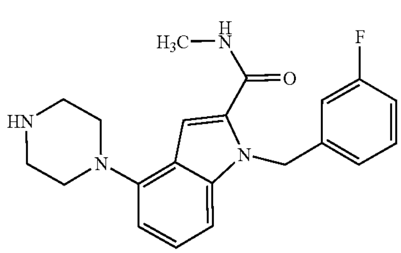 | 1-(3-Fluoro-benzyl)-4-piperazin-1-yl-1H-indole-2-carboxylic acid methylamide | 215.0-217.0 (TFA salt) |
| 27 | 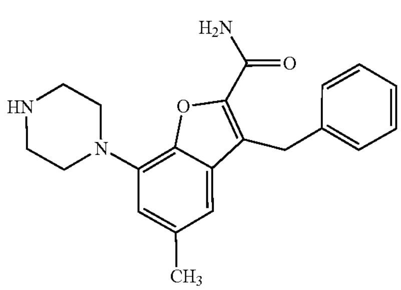 | 3-Benzyl-5-methyl-7-piperazin-1-yl-benzofuran-2-carboxylic acid amide | 227.0-228.0 (TFA salt) |

TABLE 1-continued

| # | Structure | Name (Autonom ™) | MP ° C./M + H |
|---|---|---|---|
| 28 | 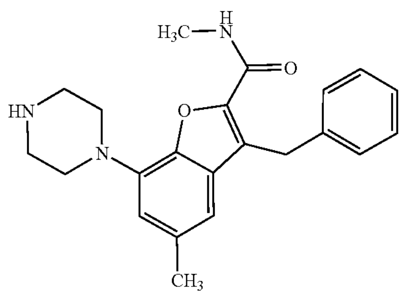 | 3-Benzyl-5-methyl-7-piperazin-1-yl-benzofuran-2-carboxylic acid methylamide | 175.4-178.7 (TFA salt) |
| 29 | 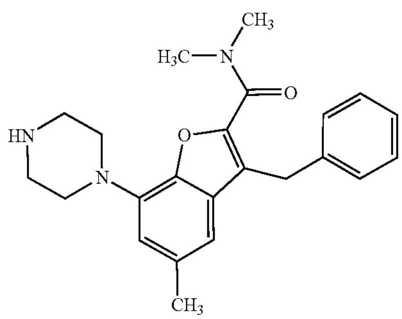 | 3-Benzyl-5-methyl-7-piperazin-1-yl-benzofuran-2-carboxylic acid dimethylamide | 176.7-177.5 (TFA salt) |
| 30 | 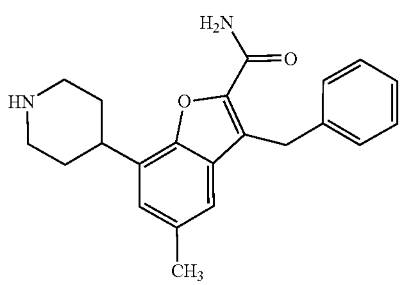 | 3-Benzyl-5-methyl-7-piperidin-4-yl-benzofuran-2-carboxylic acid amide | 216.9-218.0 (TFA salt) |
| 31 | 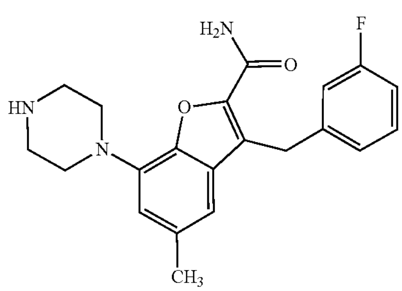 | 3-(3-Fluoro-benzyl)-5-methyl-7-piperazin-1-yl-benzofuran-2-carboxylic acid amide | 235.0-236.6 (TFA salt) |
| 32 | 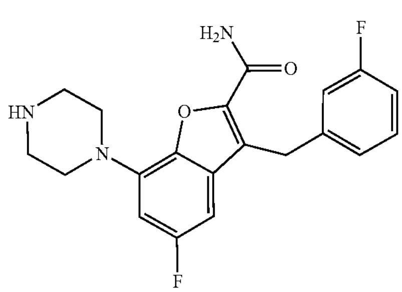 | 5-Fluoro-3-(3-fluoro-benzyl)-7-piperazin-1-yl-benzofuran-2-carboxylic acid amide | 234.9-236.0 (TFA salt) |

TABLE 1-continued

| # | Structure | Name (Autonom ™) | MP ° C./M + H |
|---|---|---|---|
| 33 | 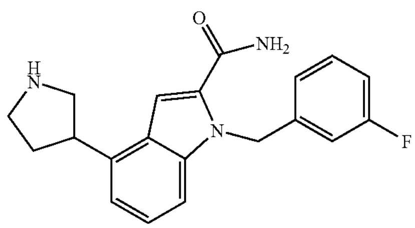 | 1-(3-Fluoro-benzyl)-4-pyrrolidin-3-yl-1H-indole-2-carboxylic acid amide | 338 |
| 34 | 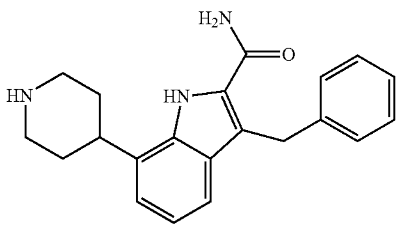 | 3-Benzyl-7-piperidin-4-yl-1H-indole-2-carboxylic acid amide | 334 |
| 35 | 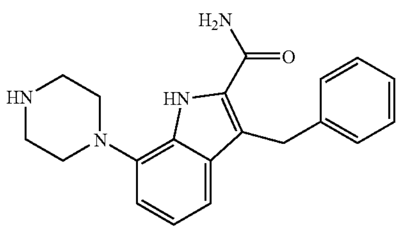 | 3-Benzyl-7-piperazin-1-yl-1H-indole-2-carboxylic acid amide | 335 |
| 36 | 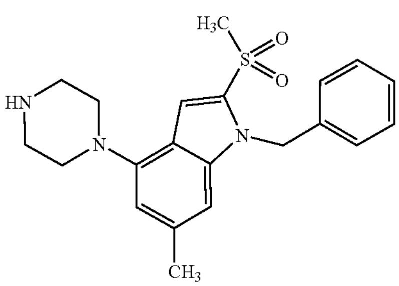 | 1-Benzyl-2-methanesulfonyl-6-methyl-4-piperazin-1-yl-1H-indole | 82.0-82.9 (TFA Salt) |
| 37 | 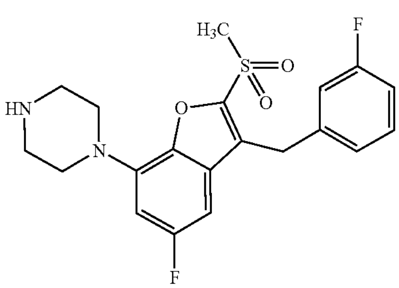 | 1-[5-Fluoro-3-(3-fluoro-benzyl)-2-methanesulfonyl-benzofuran-7-yl]-piperazine | 230.2-231.8 (TFA Salt) |
| 38 | 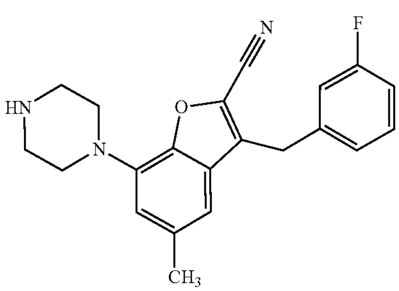 | 3-(3-Fluoro-benzyl)-5-methyl-7-piperazin-1-yl-benzofuran-2-carbonitrile | 350 |

TABLE 1-continued

| # | Structure | Name (Autonom ™) | MP ° C./M + H |
|---|---|---|---|
| 39 | 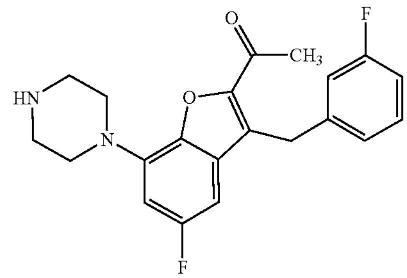 | 1-[5-Fluoro-3-(3-fluoro-benzyl)-7-piperazin-1-yl-benzofuran-2-yl]-ethanone | 371 |
| 40 | 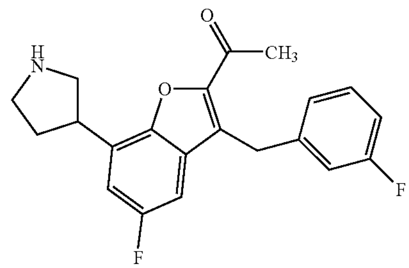 | 1-[5-Fluoro-3-(3-fluoro-benzyl)-7-pyrrolidin-3-yl-benzofuran-2-yl]-ethanon | 356 |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein PG is a protecting group, R is lower alkyl, X is a leaving group, and m, s, $R^2$, $R^3$, $R^4$, $R^8$, $R^e$ and $R^f$ are as defined herein. Numerous synthetic routes may be used in preparation of the subject compounds, and the procedure of Scheme A is only exemplary. Specific examples of the procedure of Scheme A are provided in the following Experimental section.

SCHEME A

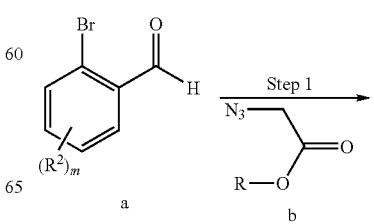

-continued

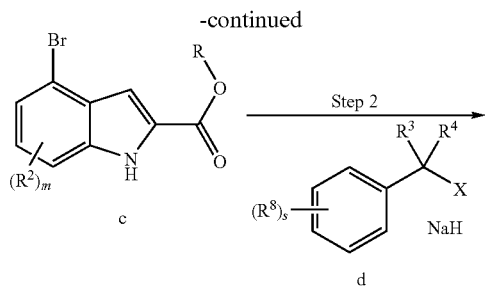

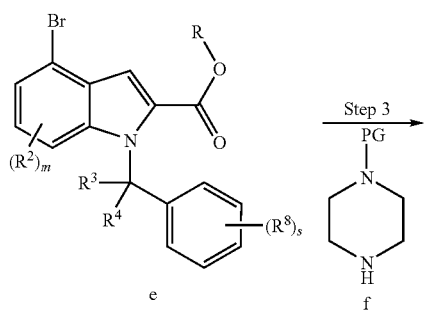

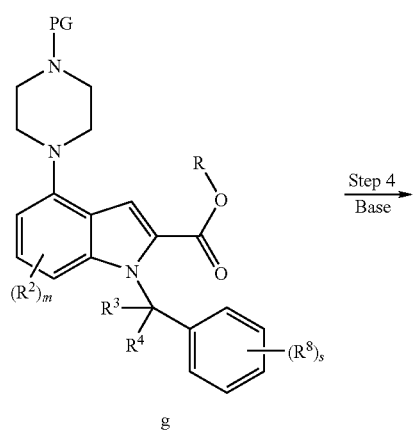

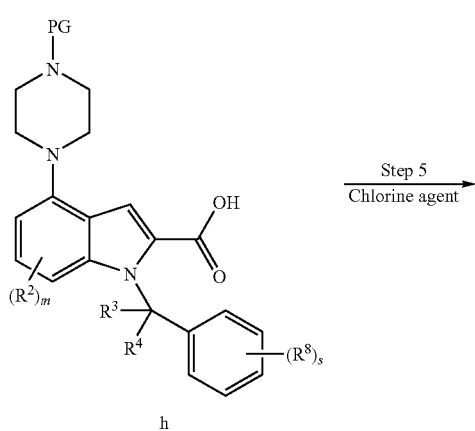

-continued

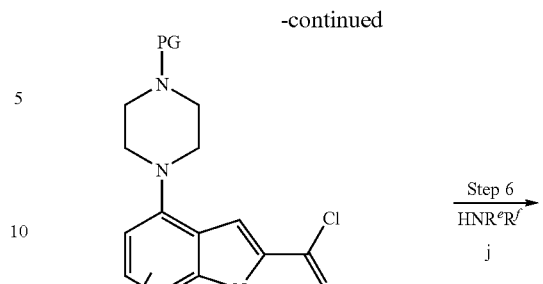

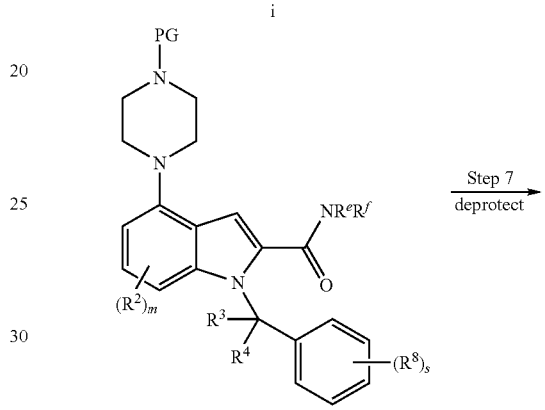

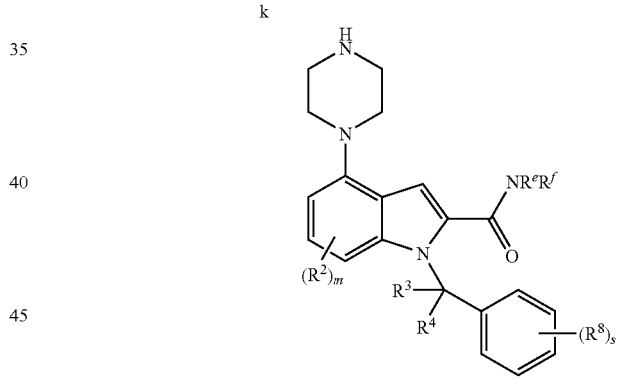

In step 1 of Scheme A, bromobenzaldehyde compound a is reacted with azido ester b under basic conditions to yield indole 2-carboxylate ester c. Compound c is then treated in step 2 with benzyl compound d in the presence of alkali metal hydride to afford 1-benzyl indole compound e. In step 3 a Buchwald reaction is carried out by reaction of compound e with protected piperazine f (other cyclic amine may be used) in the presence of suitable catalyst to provide piperazinyl indole g. The ester portion of compound g is hydrolized under basic conditions in step 4 to afford indole-2-carboxylate compound h. In step 5, indole-2-carboxylate compound h is reacted with a chlorine agent such as thionyl chloride, phosphorus oxychloride of oxalyl chloride, to afford indole-2-carboxylic acid chloride compound i. In step 6 acid chloride compound i is reacted with amine j to afford indole-2-carboxamide compound k. Compound k is then deprotected in step 7 to afford compound m, which is a compound of formula I in accordance with the invention.

Referring to Scheme B, there is shown another procedure that may be utilized to prepare compounds of the invention, with m, s, X, PG, $R^2$ and $R^8$ being as defined herein. The procedure of Scheme 3 provides compounds of formula (I) wherein X is carbon instead of nitrogen.

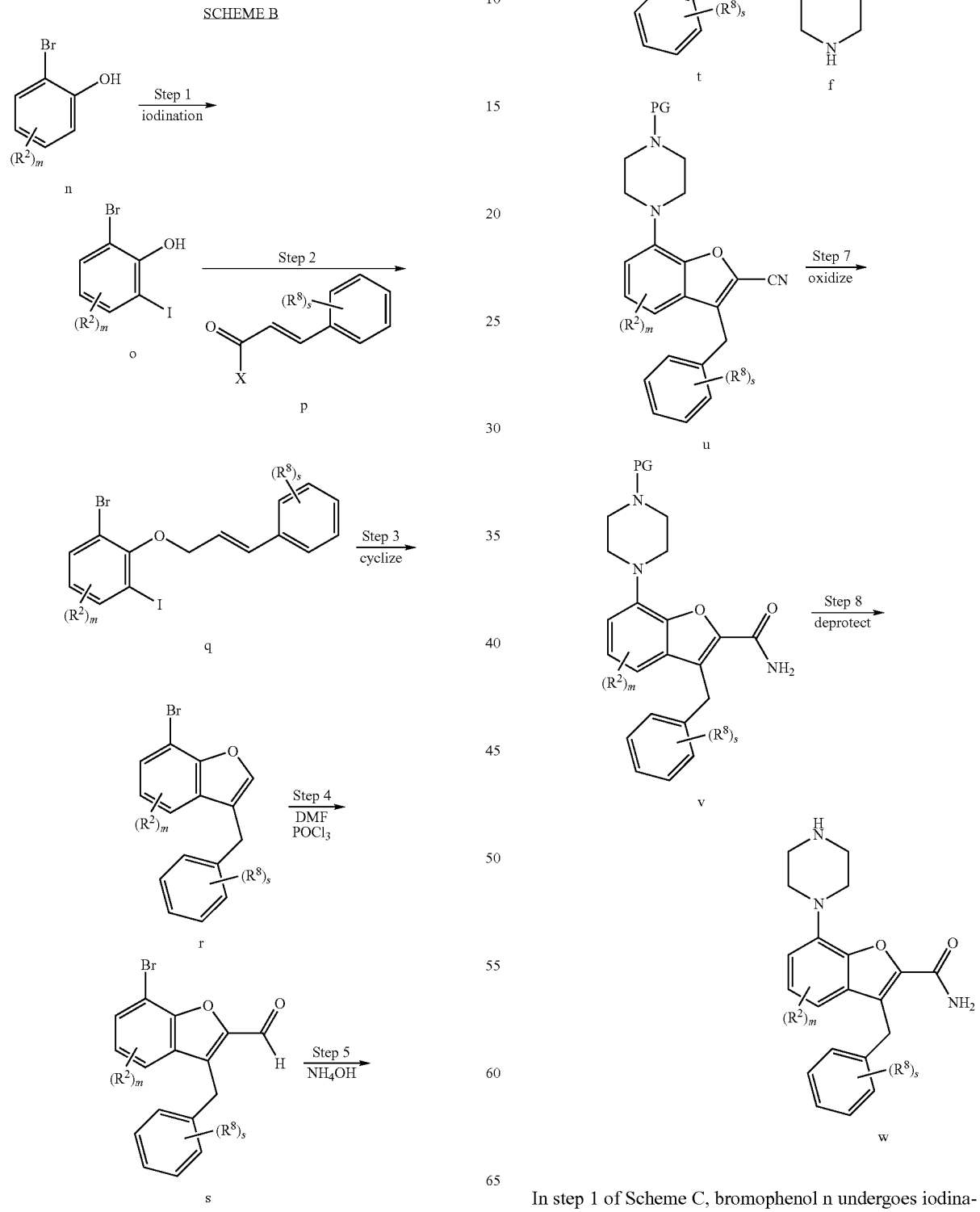

In step 1 of Scheme C, bromophenol n undergoes iodination to form bromo-iodo-phenol o. Phenol compound o is then reacted with cinnamoyl halide p in step 2 to afford phenoxy ester compound g. Compound g undergoes a cyclization in step 3 to form benzofuran compound r. In step 4 compound r is reacted with dimethyl formamide in the presence of phosphorus oxychloride to afford benzofuran-2-carboxaldehyde s. Aldehyde compound s is converted to cyano-benzofuran compound t in step 5 by reaction with aqueous ammonia. In step 6 a Buchwald reaction is carried out by reacting compound t with piperazine compound f to afford piperazinyl benzofuran u. The nitrile group of compound u undergoes oxidation in step 7 to give benzofuran carboxamide compound v. Compound v is then deprotected in step 8 to afford compound w, which is a compound of formula II in accordance with the invention.

Numerous variations are possible in the procedures of Scheme A and Scheme B and will suggest themselves to those skilled in the art. Specific details for producing compounds of formula I and formula II are described in the Examples section below.

Utility

The compounds of the invention have selective affinity for 5-HT receptors, including the 5-HT$_6$ the 5-HT$_{2A}$ receptor, or both, and as such are expected to be useful in the treatment of certain CNS disorders such as Parkinson's disease, Hunting- ton's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding, FLIPR and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

Abbreviations

BINAP 2,2'-bis(diphenylaphosphino)-1,1'-binaphthyl
BOC carboxylic acid tert-butyl ester
DCM dichloromethane/methylene chloride
DMF N,N-dimethylformamide
DMAP 4-dimethylaminopyridine
EtOAc ethyl acetate
EtOH ethanol
tBuOH tert-butanol
gc gas chromatography
HMPA hexamethylphosphoramide
hplc high performance liquid chromatography
mCPBA m-chloroperbenzoic acid
MeCN acetonitrile
NMP N-methylpyrrolidinone
TEA triethylamine
TFA trifluoroacetic acid/trifluoroacetate
THF tetrahydrofuran
LDA lithium diisopropylamine
TLC thin layer chromatography

Example 1

1-Benzyl-4-(4-methyl-piperazin-1-yl)-1H-indole-2-carboxylic Acid Amide

The synthetic procedures described in this Example were carried out according to the process shown in Scheme E.

SCHEME E

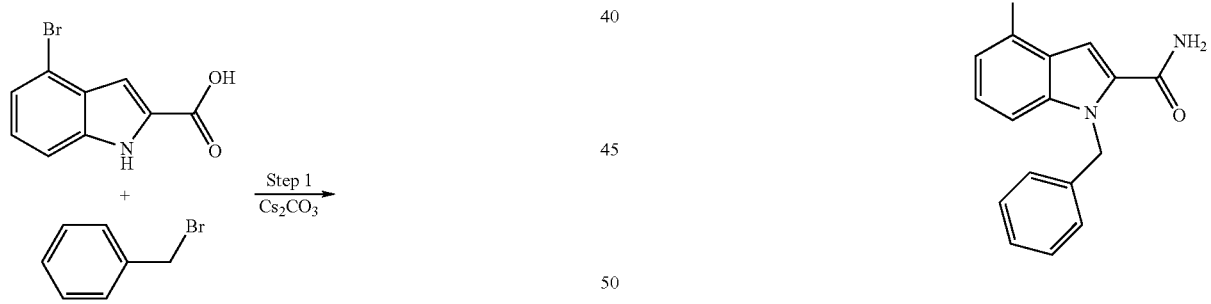

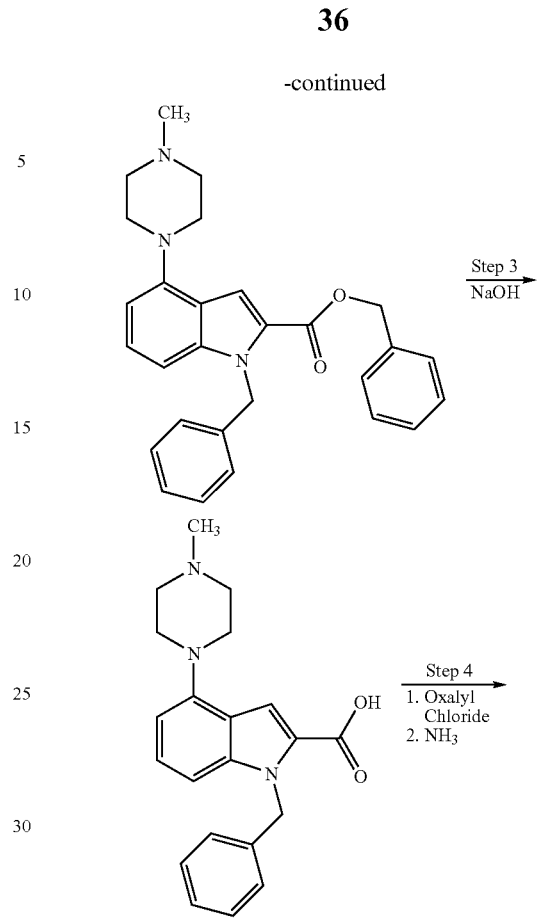

Step 1 1-Benzyl-4-bromo-1H-indole-2-carboxylic acid benzyl ester

To a solution of 4-bromo-1H-indole-2-carboxylic acid (3.78 g, 15.76 mmol) in CH$_3$CN (250 ml) were added Cs$_2$CO$_3$ (12.8 g, 39.3 mmol) and benzylbromide (4.7 ml, 39.5 mmol). After stirring at room temperature overnight, the reaction mixture was poured into a mixture of water/ethyl acetate. The organic layer was washed with water and brine. After drying over MgSO$_4$, the organic layer was concentrated in vacuo and the resulting brown residue was purified by flash chromatography to give 1-benzyl-4-bromo-1H-indole-2-carboxylic acid benzyl ester as a yellow solid (5.143 g, 77%). MS: (M+H)$^+$ 422.

Step 2 1-Benzyl-4-(4-methyl-piperazin-1-yl)-1H-indole-2-carboxylic acid benzyl ester A solution of 1-Benzyl-4-bromo-1H-indole-2-carboxylic acid benzyl ester (235 mg, 0.56 mmol) and 1-methyl-piperazine (80 ul, 0.72 mmol) in 5 ml Dioxane was added to a mixture of $Pd_2(dba)_3$ (10 mg, 0.01 mmol), BINAP (18 mg, 0.03 mmol), $Cs_2CO_3$ (547 mg, 1.68 mmol). With stirring, the solution was heated at 100° C. overnight and was allowed to cool to room temperature. The reaction mixture was filtered through celite and washed with ethyl acetate. The filtrate was concentrated in vacuo and the resulting brown residue was purified by preparative TLC (7% MeOH in $CH_2Cl_2$ containing 0.7% $NH_4OH$) to give 174 mg of 1-benzyl-4-(4-methyl-piperazin-1-yl)-1H-indole-2-carboxylic acid benzyl ester as a yellow solid (71%). MS: $(M+H)^+$ 440.3.

Step 3 1-Benzyl-4-(4-methyl-piperazin-1-yl)-1H-indole-2-carboxylic acid

To a solution of 1-benzyl-4-(4-methyl-piperazin-1-yl)-1H-indole-2-carboxylic acid benzyl ester (847 mg, 1.93 mmol) in EtOH (50 ml) was added 10 ml of 2M NaOH solution. After refluxing overnight, the reaction mixture was cooled to room temperature, and a 6M HCl solution was added slowly to adjust the pH to 0. The reaction mixture was poured into a mixture of water/ethyl acetate. The organic fraction was washed with water and brine. After drying over $MgSO_4$, the organic fraction was concentrated in vacuo to give 4-(4-tert-butoxycarbonyl-piperazin-1-yl)-1-(2-chloro-benzyl)-1H-indole-2-carboxylic acid (451 mg, 50%). MS: $(M+H)^+$ 350.

Step 4 1-Benzyl-4-(4-methyl-piperazin-1-yl)-1H-indole-2-carboxylic acid amide To a solution of 4-(4-tert-butoxycarbonyl-piperazin-1-yl)-1-(2-chloro-benzyl)-1H-indole-2-carboxylic acid (336 mg, 0.96 mmol) in $CH_2Cl_2$ were added 2M oxalyl chloride (1 ml, 2 mmol) and two drops of DMF. Gas evolution was observed. After stirring at room temperature for 30 minutes, the solvent was removed under reduced pressure. The resulting solid was dissolved in dry THF. Ammonia gas was bubbled through for 10 minutes, during which time the reaction mixture turned cloudy. A mixture of water/ethyl acetate was added to the reaction. The organic fraction was washed with water and brine. After drying over $MgSO_4$, the organic fraction was concentrated in vacuo and the resulting residue was purified by flash chromatography to give 1-benzyl-4-(4-methyl-piperazin-1-yl)-1H-indole-2-carboxylic acid amide as yellow solid (167 mg, 51%). MS: 349 $(M+H)^+$. The amide compound was dissolved in 4 ml ethanol, and an ethanolic hydrochloric acid solution (2M, 3 ml) was added. The reaction mixture was heated to 100° C. for 20 minutes, then cooled to cool to room temperature, resulting in precipitation of the hydrochloride salt.

The following compounds were prepared in a similar fashion:

1-(2-fluoro-benzyl)-4-piperazin-1-yl-1H-indole-2-carboxylic acid amide hydrochloride salt, MS: 353 $(M+H)^+$;
1-(3-fluoro-benzyl)-4-piperazin-1-yl-1H-indole-2-carboxylic acid amide hydrochloride salt, MS: 353 $(M+H)^+$;
1-(4-fluoro-benzyl)-4-piperazin-1-yl-1H-indole-2-carboxylic acid amide hydrochloride salt, MS: 353 $(M+H)^+$;
1-(3-Chloro-benzyl)-4-piperazin-1-yl-1H-indole-2-carboxylic acid amide hydrochloride salt, MS: 369 $(M+H)^+$;
1-Benzyl-4-piperazin-1-yl-1H-indole-2-carboxylic acid amide hydrochloride salt, MS: 335 $(M+H)^+$;
1-Benzyl-4-piperazin-1-yl-1H-indole-2-carboxylic acid dimethylamide hydrochloride salt;
1-Benzyl-4-piperazin-1-yl-1H-indole-2-carboxylic acid methyl amide hydrochloride salt, MS: 349 $(M+H)^+$;
1-Benzyl-4-(3-methylamino-pyrrolidin-1-yl)-1H-indole-2-carboxylic acid amide hydrochloride salt, MS: 349 $(M+H)^+$;
(1-Benzyl-4-piperazin-1-yl-1H-indol-2-yl)-piperazin-1-yl-methanone TFA salt, MS: 404 $(M+H)^+$; and
1-(3-Fluoro-benzyl)-4-piperazin-1-yl-1H-indole-2-carboxylic acid methylamide TFA salt, MS: 367 $(M+H)^+$.

Example 2

1-(3-Fluoro-benzyl)-4-(1-methyl-piperidin-4-yl)-1H-indole-2-carboxylic Acid Amide The synthetic procedures described in this Example were carried out according to the process shown in Scheme E.

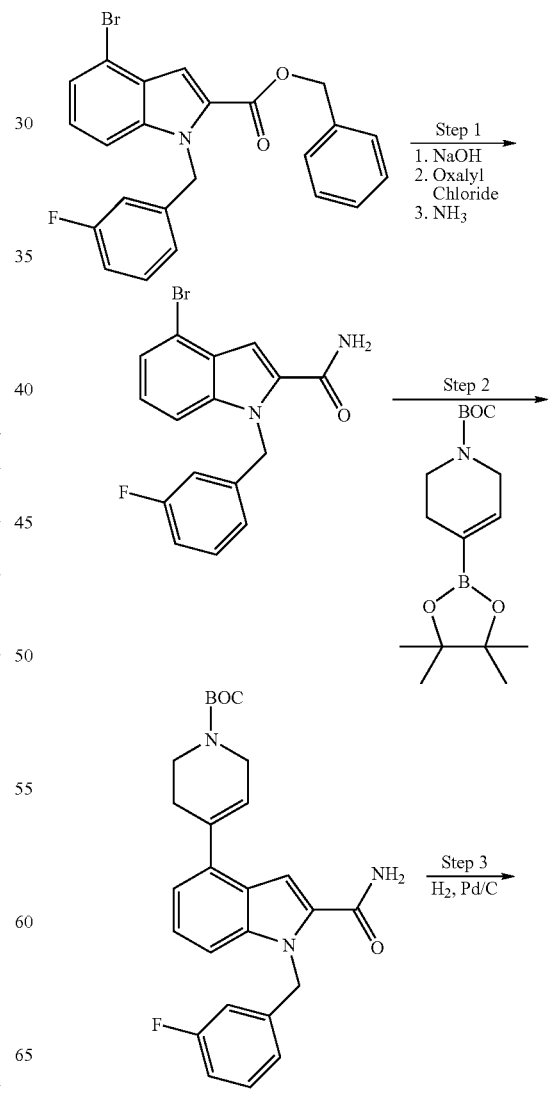

-continued

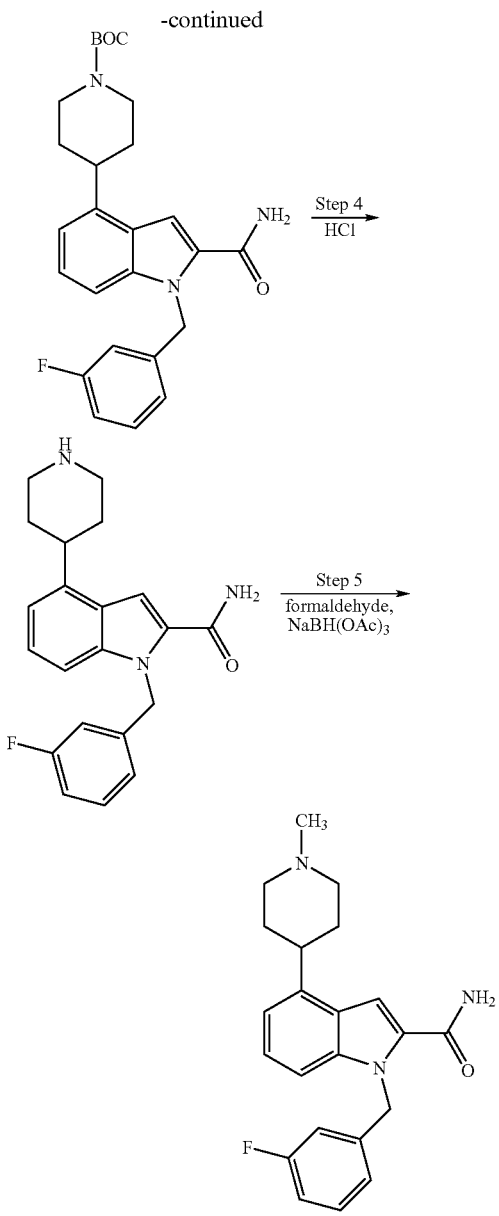

Step 1 4-Bromo-1-(3-fluoro-benzyl)-1H-indole-2-carboxylic acid amide

4-Bromo-1-(3-fluoro-benzyl)-1H-indole-2-carboxylic acid amide was prepared from 4-bromo-1-(3-fluoro-benzyl)-1H-indole-2-carboxylic acid benzyl ester by hydrolysis with ethanolic NaOH, followed by treatment with oxalyl chloride and then ammonia, as described in steps 3 and 4 of Example 1 MS: 348 (M+H)$^+$.

Step 2 4-[2-Carbamoyl-1-(3-fluoro-benzyl)-1H-indol-4-yl]-3,6-dihydro-2H-pyridine-1-carboxylic acid tert-butyl ester To a solution of 4-Bromo-1-(3-fluoro-benzyl)-1H-indole-2-carboxylic acid amide (490 mg, 1.41 mmol) in dioxane (10 ml) were added 1,1-bis(diphenylphosphino)ferrocene dichloropalladium(ii) (103 mg, 0.14 mmol), K$_2$CO$_3$ (585 mg, 4.23 mmol), and 4-(4,4,5,5-Tetramethyl-[1,3,2]dioxaborolan-2-yl)-cyclohex-3-enecarboxylic acid tert-butyl ester (523 mg, 1.69 mmol). After heating at 80° C. overnight, the reaction solution was filtered through Celite and concentrated under reduced pressure. The resulting residue was purified by flash chromatography to give 4-[2-Carbamoyl-1-(3-fluoro-benzyl)-1H-indol-4-yl]-3,6-dihydro-2H-pyridine-1-carboxylic acid tert-butyl ester as yellow solid (156 mg, 25%). MS: (M+H)$^+$ 394.2, 350.2.

Step 3 4-[2-Carbamoyl-1-(3-fluoro-benzyl)-1H-indol-4-yl]-piperidine-1-carboxylic acid tert-butyl ester 4-[2-Carbamoyl-1-(3-fluoro-benzyl)-1H-indol-4-yl]-3,6-dihydro-2H-pyridine-1-carboxylic acid tert-butyl ester (156 mg, 0.35 mmol) in EtOH (20 ml) was added to a Parr vessel containing catalytic amount of 5% Pd on carbon. The vessel was purged with H$_2$ at the pressure of 50 psi (3.45 bar). After shaking overnight, the reaction mixture was filtered through Celite and concentrated. The brown residue was purified by flash chromatography to give 4-[2-carbamoyl-1-(3-fluoro-benzyl)-1H-indol-4-yl]-piperidine-1-carboxylic acid tert-butyl ester as yellow solid (76 mg, 48%).

Step 4 1-(3-Fluoro-benzyl)-4-piperidin-4-yl-1H-indole-2-carboxylic acid amide 4-[2-Carbamoyl-1-(3-fluoro-benzyl)-1H-indol-4-yl]-piperidine-1-carboxylic acid tert-butyl ester (76 mg) was dissolved in 4 ml ethanol. To this solution was added 2 M ethanolic hydrochloric acid solution (1 ml.) The reaction mixture was heated at 100° C. for 20 minutes, at which time a crystalline solid formed. The solution was allowed to cool to room temperature and 40 mg of 1-(3-Fluoro-benzyl)-4-piperidin-4-yl-1H-indole-2-carboxylic acid amide hydrochloride salt was collected as a yellow powder. MS: 352 (M+H)$^+$.

The following compounds were prepared in a similar fashion:
1-Benzyl-4-piperidin-4-yl-1H-indole-2-carboxylic acid amide hydrochloride salt, MS: 334 (M+H)$^+$;
1-Benzyl-4-piperidin-4-yl-1H-indole-2-carboxylic acid dimethylamide hydrochloride salt, MS: 334 (M+H)$^+$;
1-(2-Fluoro-benzyl)-4-piperidin-4-yl-1H-indole-2-carboxylic acid amide hydrochloride salt, MS: 352 (M+H)$^+$;
1-(4-Fluoro-benzyl)-4-piperidin-4-yl-1H-indole-2-carboxylic acid amide hydrochloride salt, MS: 352 (M+H)$^+$;
1-(2-chloro-benzyl)-4-piperidin-4-yl-1H-indole-2-carboxylic acid amide hydrochloride salt, MS: 368 (M+H)$^+$;
1-(3-chloro-benzyl)-4-piperidin-4-yl-1H-indole-2-carboxylic acid amide hydrochloride salt, MS: 368 (M+H)$^+$;
1-(4-chloro-benzyl)-4-piperidin-4-yl-1H-indole-2-carboxylic acid amide hydrochloride salt, MS: 368 (M+H)$^+$;
1-(2,3-Difluoro-benzyl)-4-piperidin-4-yl-1H-indole-2-carboxylic acid amide hydrochloride salt, MS: 370 (M+H)$^+$;
1-(3,4-Difluoro-benzyl)-4-piperidin-4-yl-1H-indole-2-carboxylic acid amide hydrochloride salt, MS: 370 (M+H)$^+$; and
1-(3,5-Difluoro-benzyl)-4-piperidin-4-yl-1H-indole-2-carboxylic acid amide hydrochloride salt, MS: 370 (M+H)$^+$.

Step 5 1-(3-Fluoro-benzyl)-4-(1-methyl-piperidin-4-yl)-1H-indole-2-carboxylic acid amide To a solution of 1-(3-Fluoro-benzyl)-4-piperidin-4-yl-1H-indole-2-carboxylic acid amide (50 mg, 0.14 mmol) in CH$_2$Cl$_2$ (5 ml) were added formaldehyde (20 μl, 0.24 mmol, 37% in H$_2$O solution) and NaBH(OAc)$_3$ (74 mg, 0.35 mmol).

After stirring at room temperature for 4 hours, the reaction mixture was added to a saturated solution of sodium bicarbonate, followed by a mixture of $CH_2Cl_2/H_2O$. The organic fraction was separated, washed with water and brine. After drying over $MgSO_4$, the organic fraction was concentrated in vacuo to give 1-(3-Fluoro-benzyl)-4-(1-methyl-piperidin-4-yl)-1H-indole-2-carboxylic acid amide as a brown oil. This oil was dissolved in 4 ml ethanol, and 2 M ethanolic hydrochloric acid solution (1 ml) was added. The reaction mixture is heated at 100° C. for 20 minutes, then cooled to room temperature, and 14 mg of 1-(3-Fluoro-benzyl)-4-(1-methyl-piperidin-4-yl)-1H-indole-2-carboxylic acid amide hydrochloride salt was collected. MS: 366 (M+H)$^+$.

Example 3

1-Benzyl-6-fluoro-4-piperazin-1-yl-1H-indole-2-carboxylic Acid Amide

The synthetic procedures described in this Example were carried out according to the process shown in Scheme E.

SCHEME

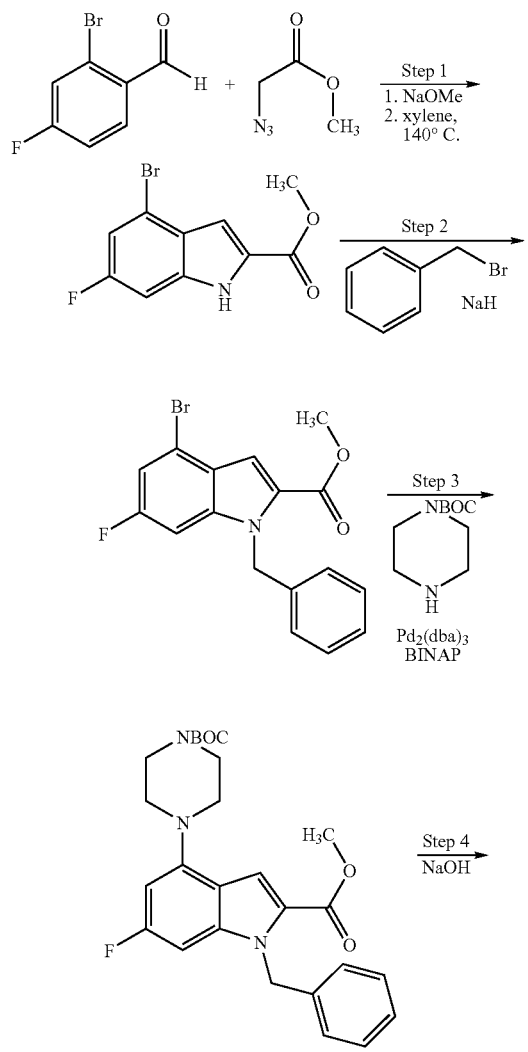

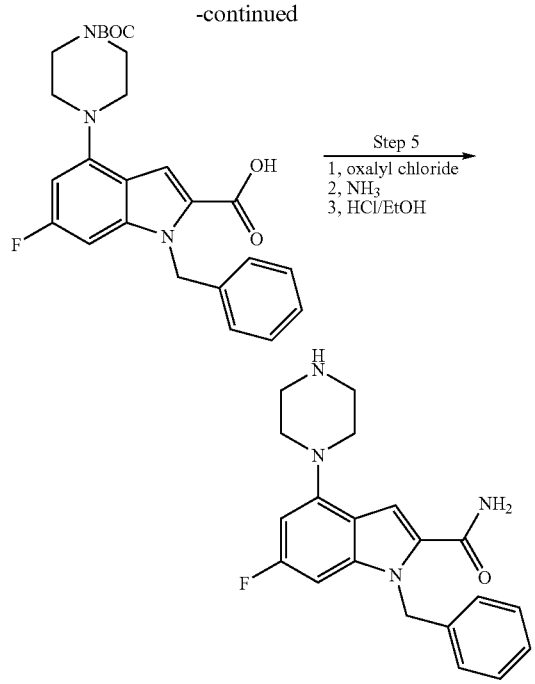

Step 1 4-Bromo-6-fluoro-1H-indole-2-carboxylic acid methyl ester

Dry methanol (5 ml) and NaOMe (0.9 ml, 3.93 mmol, 25% wt in MeOH) were added to a three-neck flask equipped with stirrer, low-temperature thermometer, and nitrogen line. The resulting solution was cooled in a dry ice/$CH_3CN$ bath to −40° C. A solution of 2-bromo-4-fluoro-benzaldehyde (195 mg, 0.96 mmol) and methyl azidoacetate (450 mg, 3.9 mmol) in dry MeOH (5 ml) was added dropwise. The mixture was allowed to stir at −40° C. for 30 minutes before warming up to room temperature. After stirring another 3 hours, the reaction solvent was removed under reduced pressure. The residue was added to xylene (15 ml), and the organic phase was washed with $H_2O$, brine, followed by drying over $MgSO_4$. The resulting solution was added dropwise to a flask of xylene (30 ml) and the solution was heated at reflux overnight. After cooling to room temperature, the reaction mixture was washed with $H_2O$, and xylene was removed under reduced pressure to give 4-bromo-6-fluoro-1H-indole-2-carboxylic acid methyl ester as a white solid (178 mg, 68%). MS: 272.1 (M−H)$^−$.

Step 2
1-Benzyl-4-bromo-6-fluoro-1H-indole-2-carboxylic acid methyl ester

To a solution of 4-bromo-6-fluoro-1H-indole-2-carboxylic acid methyl ester (178 mg, 0.65 mmol) in 5 ml anhydrous dimethylformanide was added sodium hydride (52 mg of a 60% suspension in mineral oil, 1.3 mmol) portionwise at 0° C. The solution was stirred with a magnetic stirrer at 0° C. for 20 minutes. Benzyl bromide (0.17 ml, 1.43 mmol) was added in one portion and the reaction mixture was stirred at 0° C. for 30 minutes. The solution was allowed to warm to room temperature and the reaction mixture was partitioned between water and ethyl acetate. The aqueous layer was extracted with ethyl acetate and the combined organic fractions were washed with water and brine. After drying over MgSO₄, the organic fraction was concentrated in vacuo and resulting brown residue was purified by Preparative TLC (10% Ethyl acetate/Hexane) to give 80 mg 1-Benzyl-4-bromo-6-fluoro-1H-indole-2-carboxylic acid methyl ester as a yellow solid (34%). ¹H NMR (CDCl₃, 300 MHz) δ: 3.89 (s, 3H), 5.78 (s, 2H), 7.17 (m, 8H).

Step 3 1-Benzyl-4-(4-tert-butoxycarbonyl-piperazin-1-yl)-6-fluoro-1H-indole-2-carboxylic acid methyl ester 1-Benzyl-4-(4-tert-butoxycarbonyl-piperazin-1-yl)-6-fluoro-1H-indole-2-carboxylic acid methyl ester was prepared using the procedure of step 2 of Example 1, but replacing 1-methyl-piperazine with 1-Boc-piperazine. MS: 468.3 (M+H)⁺.

Step 4 1-Benzyl-4-(4-tert-butoxycarbonyl-piperazin-1-yl)-6-fluoro-1H-indole-2-carboxylic acid 1-Benzyl-4-(4-tert-butoxycarbonyl-piperazin-1-yl)-6-fluoro-1H-indole-2-carboxylic acid methyl ester was hydrolized to 1-benzyl-4-(4-tert-butoxycarbonyl-piperazin-1-yl)-6-fluoro-1H-indole-2-carboxylic acid using ethanolic NaOH as described in step 3 of Example 1. MS: 454.3 (M+H)⁺.

Step 5 1-Benzyl-6-fluoro-4-piperazin-1-yl-1H-indole-2-carboxylic acid amide

1-Benzyl-4-(4-tert-butoxycarbonyl-piperazin-1-yl)-6-fluoro-1H-indole-2-carboxylic acid amide was prepared from 1-benzyl-4-(4-tert-butoxycarbonyl-piperazin-1-yl)-6-fluoro-1H-indole-2-carboxylic acid using the procedure of step 4 of Example 1. The 1-benzyl-4-(4-tert-butoxycarbonyl-piperazin-1-yl)-6-fluoro-1H-indole-2-carboxylic acid amide was treated with ethanolic HCl as described in step 4 of Example 2 to give 1-benzyl-6-fluoro-4-piperazin-1-yl-1H-indole-2-carboxylic acid amide as a hydrochloride salt. MS: 353 (M+H)⁺.

Example 4

1-Benzyl-6-fluoro-4-piperidin-4-yl-1H-indole-2-carboxylic Acid Amide

The synthetic procedures described in this Example were carried out according to the process shown in Scheme F.

SCHEME F

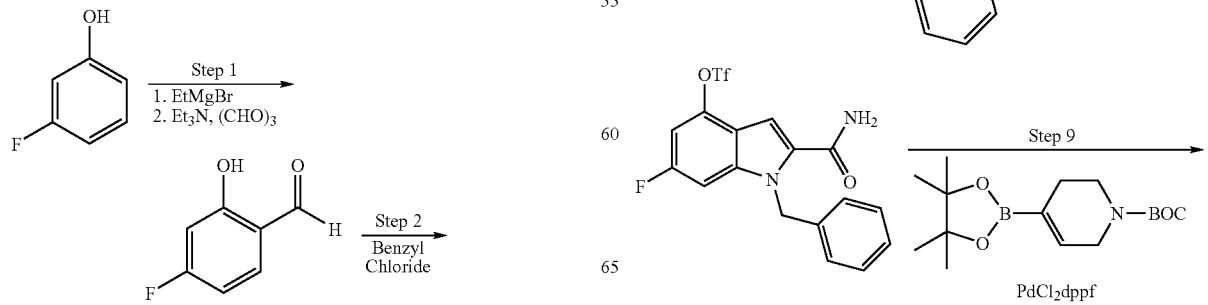

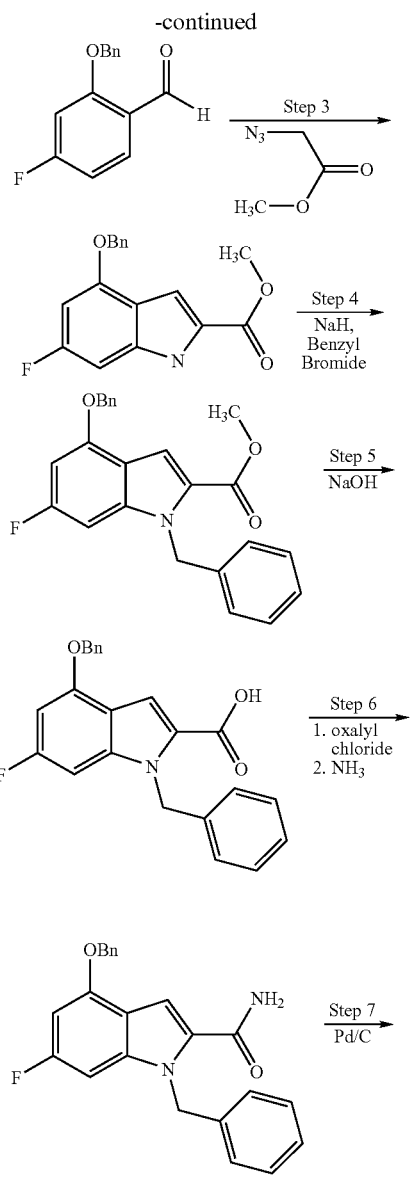

-continued

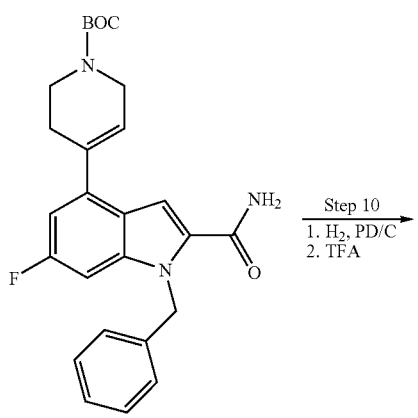

Step 10
1. H₂, PD/C
2. TFA

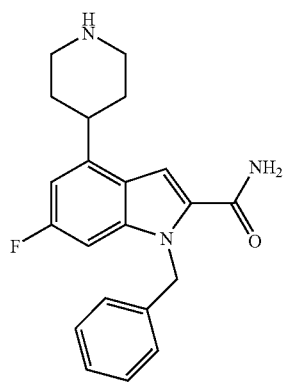

Step 1 4-Fluoro-2-hydroxy-benzaldehyde

To a solution of 3-fluorophenol (1 ml, 11 mmol) in THF (20 ml) in a three-neck flask was added ethylmagnesium bromide (5.5 ml, 5.5 mmol, 1M in THF). After stirring at room temperature for 2 hours, benzene was added to the reaction mixture and THF was removed by distillation at 80° C. Additional benzene (50 ml) was added to the reaction, followed by NEt₃ (2.3 ml, 16.5 mmol) and paraformaldehyde (1 g, 33.3 mmol). After heating at reflux for 3 hours, the reaction mixture was allowed to cool to room temperature and was poured into 250 ml of 10% HCl. EtOAc was added and the organic layer was separated and washed with H₂O. After drying over MgSO₄, the solvent was removed under reduced pressure. The resulting residue was purified by flash chromatography to give 4-fluoro-2-hydroxy-benzaldehyde as a white solid (560 mg, 36%), $^1$H NMR (CDCl₃, 300 MHz) δ: 6.71 (m, 2H), 7.56 (dd, 1H, J=6.3 Hz, 8.6 Hz), 9.84 (s, 1H), 11.36 (s, 1H).

Step 2 2-Benzyloxy-4-fluoro-benzaldehyde

To a solution of 4-fluoro-2-hydroxy-benzaldehyde (560 mg, 4 mmol) in DMF (10 ml) were added benzyl chloride (0.5 ml, 4.33 mmol), and K₂CO₃ (860 mg, 6.22 mmol). After heating at reflux for an hour, the reaction mixture was allowed to cool to room temperature and was poured into a mixture of EtOAc/H₂O. The organic layer was separated, washed with H₂O and dried over MgSO₄. The resulting oil was purified by flash chromatography to give 2-benzyloxy-4-fluoro-benzaldehyde as pale oil (628 mg, 68%), $^1$H NMR (CDCl3, 300 MHz) δ: 5.17 (s, 2H), 6.74 (m, 2H), 7.36 (m, 5H), 7.88 (m, 1H), 10.51 (s, 1H).

Step 3 4-Benzyloxy-6-fluoro-1H-indole-2-carboxylic acid methyl ester

4-Benzyloxy-6-fluoro-1H-indole-2-carboxylic acid methyl ester was prepared from 2-benzyloxy-4-fluoro-benzaldehyde using the procedure of step 1 of Example 3. $^1$H NMR (DMSO, 300 MHz) δ: 3.85 (s, 3H), 5.26 (s, 2H), 6.62 (dd, 1H, J=2 Hz, 12 Hz), 6.76 (m, 1H), 7.13 (m, 1H), 7.42 (m, 5H).

Step 4 1-Benzyl-4-benzyloxy-6-fluoro-1H-indole-2-carboxylic acid methyl ester 1-Benzyl-4-benzyloxy-6-fluoro-1H-indole-2-carboxylic acid methyl ester was prepared from 4-benzyloxy-6-fluoro-1H-indole-2-carboxylic acid methyl ester using the procedure of step 2 of Example 3. MS: 390.2 (M+H)⁺.

Step 5 1-Benzyl-4-benzyloxy-6-fluoro-1H-indole-2-carboxylic acid

1-Benzyl-4-benzyloxy-6-fluoro-1H-indole-2-carboxylic acid was prepared from 1-benzyl-4-benzyloxy-6-fluoro-1H-indole-2-carboxylic acid methyl ester following the procedure of step 3 of Example 1. MS: 376.1 (M+H)⁺.

Step 6 1-Benzyl-4-benzyloxy-6-fluoro-1H-indole-2-carboxylic acid amide

1-Benzyl-4-benzyloxy-6-fluoro-1H-indole-2-carboxylic acid was converted to 1-benzyl-4-benzyloxy-6-fluoro-1H-indole-2-carboxylic acid amide using the procedure of step 4 of Example 1. $^1$H NMR (CDCl₃, 300 MHz) δ: 5.17 (s, 2H), 5.78 (s, 2H), 6.41 (dd, 1H, J=1.90 Hz, 11.46 Hz), 6.64 (m, 1H), 7.28 (m, 6H).

Step 7 1-Benzyl-6-fluoro-4-hydroxy-1H-indole-2-carboxylic acid amide

1-Benzyl-4-benzyloxy-6-fluoro-1H-indole-2-carboxylic acid amide (570 mg, 1.52 mmol) in EtOH (20 ml) was added to a Parr vessel containing catalytic amount of 5% Pd on carbon. The vessel was purged with H₂ at the pressure of 3.45 Bar. After shaking overnight, the reaction mixture was filtered through Celite and concentrated under reduced pressure. The residue was purified by flash chromatography to give 1-benzyl-6-fluoro-4-hydroxy-1H-indole-2-carboxylic acid amide as yellow solid (312 mg, 72%). MS: 285.2 (M+H)⁺.

Step 8 Trifluoro-methanesulfonic acid 1-benzyl-2-carbamoyl-6-fluoro-1H-indol-4-yl ester To a solution of 1-benzyl-6-fluoro-4-hydroxy-1H-indole-2-carboxylic acid amide (312 mg, 1.10 mmol) in CH₂Cl₂ (10 ml) was added pyridine (0.1 ml, 1.24 mmol) and trifluoromethanesulfonic anhydride (0.2 ml, 1.18 mmol). After stirring at room temperature for 30 minutes, the reaction mixture was poured into the mixture of EtOAc/H₂O. The organic fraction was separated and washed with water and brine. After drying over MgSO₄, the organic fraction was concentrated in vacuo and the resulting residue was purified by flash chromatography to give trifluoro-methanesulfonic acid 1-benzyl-2- carbamoyl-6-fluoro-1H-indol-4-yl ester as yellow solid (200 mg, 44%). MS: (M+H)+ 415.2.

Step 9 4-(1-Benzyl-2-carbamoyl-6-fluoro-1H-indol-4-yl)-3,6-dihydro-2H-pyridine-1-carboxylic acid tert-butyl ester 4-(1-Benzyl-2-carbamoyl-6-fluoro-1H-indol-4-yl)-3,6-dihydro-2H-pyridine-1-carboxylic acid tert-butyl ester was prepared from trifluoro-methanesulfonic acid 1-benzyl-2-carbamoyl-6-fluoro-1H-indol-4-yl ester and 4-(4,4,5,5'-Tetramethyl-[1,3,2]dioxaborolan-2-yl)-cyclohex-3-enecarboxylic acid tert-butyl ester using the procedure of step 2 of Example 2.

Step 10 1-Benzyl-6-fluoro-4-piperidin-4-yl-1H-indole-2-carboxylic acid amide 1-Benzyl-6-fluoro-4-piperidin-4-yl-1H-indole-2-carboxylic acid amide was prepared as trifluoroacetate salt by hydrogenation of 4-(1-Benzyl-2-carbamoyl-6-fluoro-1H-indol-4-yl)-3,6-dihydro-2H-pyridine-1-carboxylic acid tert-butyl ester, followed by deprotection with trifluoroacetic acid, using the procedure of steps 3 and 4 of Example 2. MS: (M+H)+ 352.

Example 5

3-Benzyl-7-piperidin-4-yl-1H-indole-2-carboxylic Acid Amide

The synthetic procedures described in this Example were carried out according to the process shown in Scheme G.

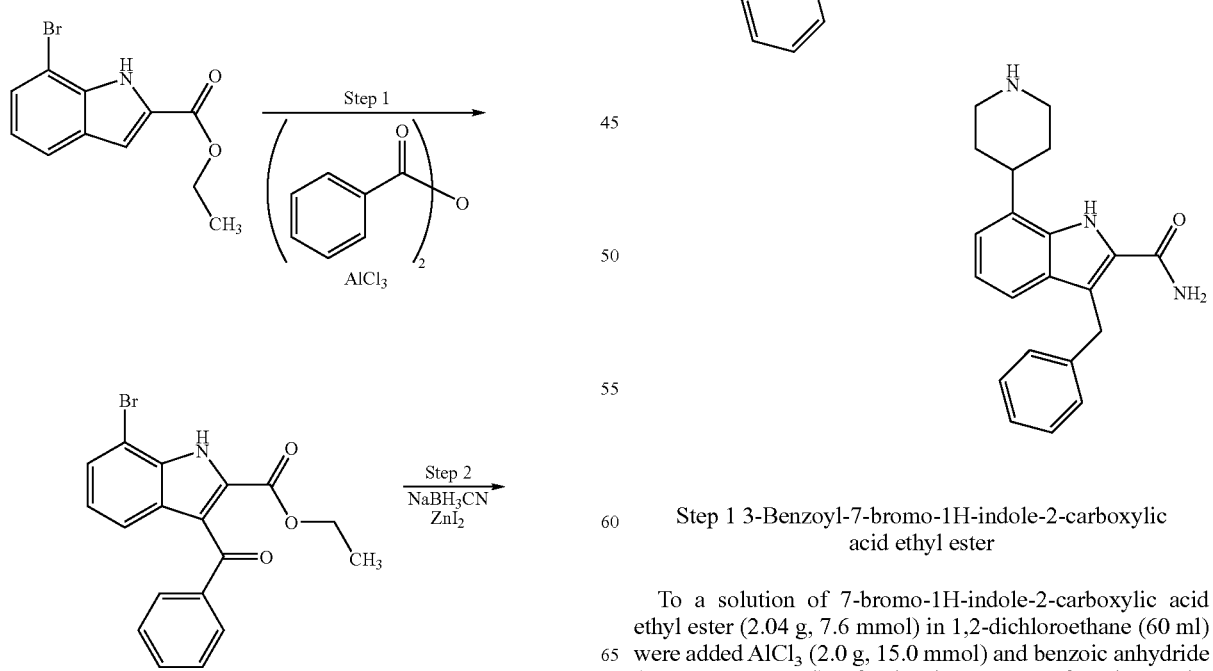

Step 1 3-Benzoyl-7-bromo-1H-indole-2-carboxylic acid ethyl ester

To a solution of 7-bromo-1H-indole-2-carboxylic acid ethyl ester (2.04 g, 7.6 mmol) in 1,2-dichloroethane (60 ml) were added AlCl₃ (2.0 g, 15.0 mmol) and benzoic anhydride (3.45 g, 15.2 mmol). After heating at 90° C. for 2 hours, the reaction mixture was poured into a mixture of EtOAc/H₂O.

The organic fraction was separated and washed with water and brine. After drying over MgSO$_4$, the organic fraction was concentrated in vacuo and the resulting residue was purified by flash chromatography to give b-Benzoyl-7-bromo-1H-indole-2-carboxylic acid ethyl ester as yellow solid (~100%). MS: (M+H)$^+$ 374.1.

Step 2 Benzyl-7-bromo-1H-indole-2-carboxylic acid ethyl ester

To a solution of 3-benzoyl-7-bromo-1H-indole-2-carboxylic acid ethyl ester (2.4 g, 6.45 mmol) in 1,2-dichloroethane (80 ml) was added NaBH$_3$CN (3.24 g, 51.6 mmol) and ZnI$_2$ (6.18 g, 19.4 mmol). After stirring at room temperature for 30 minutes, the reaction mixture was poured into a mixture of EtOAc/H$_2$O. The organic layer was separated and washed with water and brine. After drying over MgSO$_4$, the organic fraction was concentrated in vacuo and the resulting residue was purified by flash chromatography to give 3-benzyl-7-bromo-1H-indole-2-carboxylic acid ethyl ester as yellow solid (696 mg, 30%). $^1$H NMR (CDCl$_3$, 300 MHz) δ: 1.39 (t, 3H, J=7.13 Hz), 4.43 (q, 2H, J=7.13 Hz), 4.49 (s, 2H), 6.98 (t, 1H, J=7.8 Hz), 7.22 (m, 5H), 7.46 (d, 1H, J=7.60 Hz), 7.54 (d, 1H, J=8.10 Hz).

Step 3 3-Benzyl-7-(1-tert-butoxycarbonyl-1,2,3,6-tetrahydro-pyridin-4-yl)-1H-indole-2-carboxylic acid ethyl ester 3-Benzyl-7-(1-tert-butoxycarbonyl-1,2,3,6-tetrahydro-pyridin-4-yl)-1H-indole-2-carboxylic acid ethyl ester was prepared from 3-benzyl-7-bromo-1H-indole-2-carboxylic acid ethyl ester and 4-(4,4,5,5-Tetramethyl-[1,3,2]dioxaborolan-2-yl)-cyclohex-3-enecarboxylic acid tert-butyl ester using the procedure of step 2 of Example 2.

Step 4 3-Benzyl-7-(1-tert-butoxycarbonyl-piperidin-4-yl)-1H-indole-2-carboxylic acid ethyl ester 3-Benzyl-7-(1-tert-butoxycarbonyl-piperidin-4-yl)-1H-indole-2-carboxylic acid ethyl ester was prepared by hydrogenation of 3-benzyl-7-(1-tert-butoxycarbonyl-1,2,3,6-tetrahydro-pyridin-4-yl)-1H-indole-2-carboxylic acid ethyl ester using the procedure of step 3 of Example 2.

Step 5 3-Benzyl-7-piperidin-4-yl-1H-indole-2-carboxylic acid amide

3-Benzyl-7-piperidin-4-yl-1H-indole-2-carboxylic acid amide was prepared as a TFA salt from 3-Benzyl-7-(1-tert-butoxycarbonyl-piperidin-4-yl)-1H-indole-2-carboxylic acid ethyl ester as a trifluoroacetate by following the procedure of step 4 of Example 1 and step 4 of Example 2. MS: (M+H)$^+$ 334.

Example 6

3-Benzyl-2-methanesulfonyl-7-piperazin-1-yl-1H-indole

The synthetic procedures described in this Example were carried out according to the process shown in Scheme H.

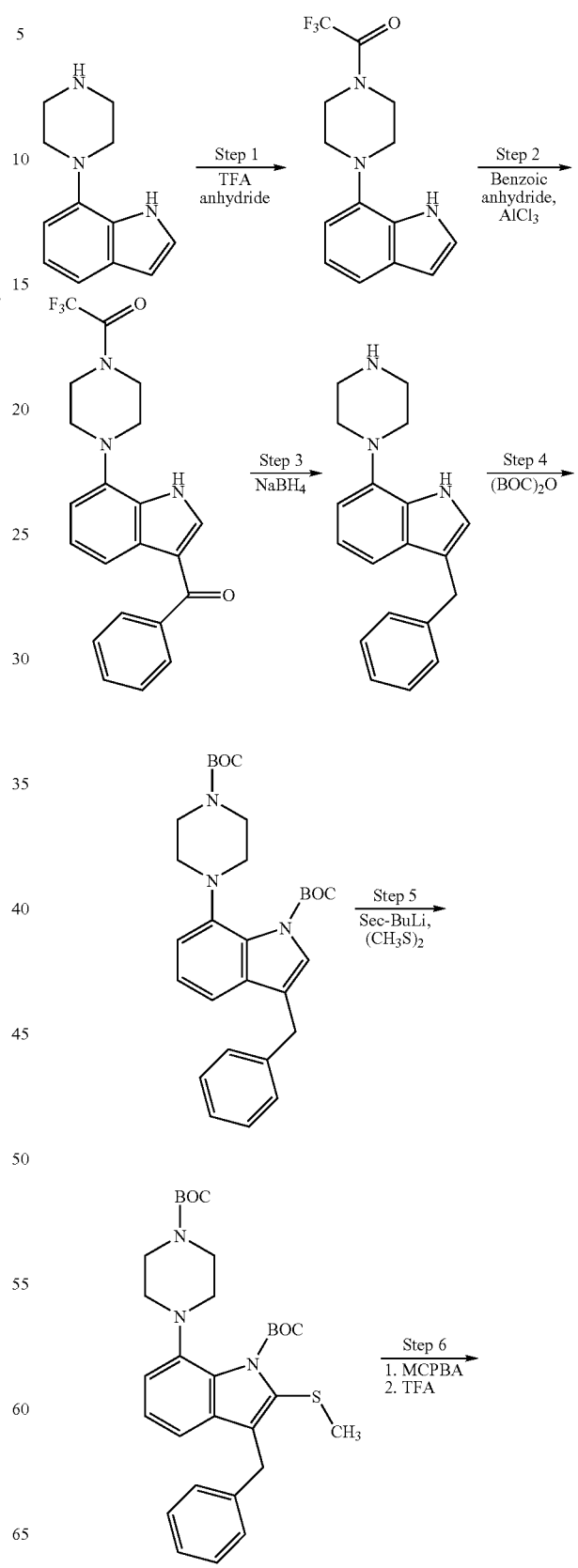

SCHEME H

-continued

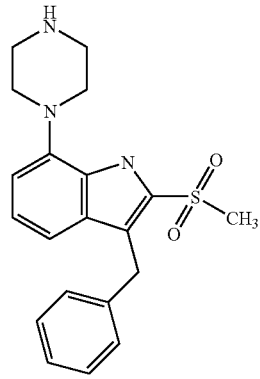

Step 1 2,2,2-Trifluoro-1-[4-(1H-indol-7-yl)-piperazin-1-yl]-ethanone

To a solution of 7-piperazin-1-yl-1H-indole (384 mg, 1.9 mmol) in $CH_2Cl_2$ (20 ml) were added TFA anhydride (0.26 ml, 1.9 mmol) and $NEt_3$ (0.53 ml, 3.8 mmol). After stirring at room temperature for half an hour, the reaction was poured into a mixture of $EtOAc/H_2O$. The organic layer was separated and washed with water and brine. After drying over $MgSO_4$, the organic fraction was concentrated in vacuo and the resulting residue was purified by flash chromatography to give 2,2,2-Trifluoro-1-[4-(1H-indol-7-yl)-piperazin-1-yl]-ethanone as white solid (462 mg, 82%). MS: $(M+H)^+$ 298.2.

Step 2 1-[4-(3-Benzoyl-1H-indol-7-yl)-piperazin-1-yl]-2,2,2-trifluoro-ethanone To a solution of 2,2,2-trifluoro-1-[4-(1H-indol-7-yl)-piperazin-1-yl]-ethanone (462 mg, 1.55 mmol) in $CH_2ClCH_2Cl$ (20 ml) were added benzoic anhydride (703 mg, 3.1 mmol) and $AlCl_3$ (414 mg, 3.1 mmol). After stirring at 90° C. for 30 minutes the reaction mixture was allowed to cool to room temperature and poured into a mixture of $EtOAc/H_2O$. The organic layer was separated and washed with water and brine. After drying over $MgSO_4$, the organic fraction was concentrated in vacuo and the resulting residue was purified by flash chromatography to give 1-[4-(3-Benzoyl-1H-indol-7-yl)-piperazin-1-yl]-2,2,2-trifluoro-ethanone as a yellow solid (475 mg, 76%). MS: $(M+H)^+$ 402.2.

Step 3 3-Benzyl-7-piperazin-1-yl-1H-indole

To a solution of 1-[4-(3-benzoyl-1H-indol-7-yl)-piperazin-1-yl]-2,2,2-trifluoro-ethanone (638 mg, 1.59 mmol) in isopropanol (30 ml) was added $NaBH_4$ (0.12 g, 3.17 mmol). After heating at reflux for 3 days, the reaction mixture was allowed to cool to room temperature and poured into a mixture of $EtOAc/H_2O$. The organic layer was separated and washed with water and brine. After drying over $MgSO_4$, the organic fraction was concentrated in vacuo to give crude 3-benzyl-7-piperazin-1-yl-1H-indole as an oil (586 mg) which was used without further purification.

Step 4 3-Benzyl-7-(4-tert-butoxycarbonyl-piperazin-1-yl)-indole-1-carboxylic acid tert-butyl ester To a solution of crude 3-benzyl-7-piperazin-1-yl-1H-indole (586 mg) in THF (30 ml) was added $(BOC)_2O$ (700 mg) and DMAP (2 mg). After stirring at room temperature for an hour, the reaction mixture was poured into mixture of $EtOAc/H_2O$. The organic layer was separated and washed with water and brine. After drying over $MgSO_4$, the organic fraction was concentrated in vacuo and the resulting brown residue was purified by flash chromatography to give 3-Benzyl-7-(4-tert-butoxycarbonyl-piperazin-1-yl)-indole-1-carboxylic acid tert-butyl ester as a yellow solid (400 mg, 51%). MS: $(M+H)^+$ 492.2.

Step 5 3-Benzyl-7-(4-tert-butoxycarbonyl-piperazin-1-yl)-2-methylsulfanyl-indole-1-carboxylic acid tert-butyl ester A solution of 3-benzyl-7-(4-tert-butoxycarbonyl-piperazin-1-yl)-indole-1-carboxylic acid tert-butyl ester (186 mg, 0.38 mmol) in THF (5 ml) was cooled to −78° C., and Sec-BuLi (1.4 ml, 1.4 M in cyclohexane) was added. After stirring at −78° C. for 20 minutes, 1 ml of dimethyl sulfide was added and the reaction was allowed to warm up to room temperature for 30 minutes. $H_2O$ was slowly added, followed by EtOAC. The organic layer was separated and washed with water and brine. After drying over $MgSO_4$, the organic fraction was concentrated in vacuo to give crude 3-benzyl-7-(4-tert-butoxycarbonyl-piperazin-1-yl)-2-methylsulfanyl-indole-1-carboxylic acid tert-butyl ester as an oil (277 mg), which was used without further purification.

Step 6 3-Benzyl-2-methanesulfonyl-7-piperazin-1-yl-1H-indole

To a solution of 3-benzyl-7-(4-tert-butoxycarbonyl-piperazin-1-yl)-2-methylsulfanyl-indole-1-carboxylic acid tert-butyl ester (277 mg) in $CH_2Cl_2$ (10 ml) was added MCPBA (296 mg) at 0° C. The reaction was allowed to warm up to room temperature overnight. After adding 150 mg of $PPh_3$, the reaction was stirred for another 30 minutes and was then poured into a mixture of $EtOAc/H_2O$. The organic layer was separated and washed with water and brine. After drying over $MgSO_4$, the organic fraction was concentrated in vacuo and the resulting residue was purified by flash chromatography to give 3-Benzyl-7-(4-tert-butoxycarbonyl-piperazin-1-yl)-2-methanesulfonyl-indole-1-carboxylic acid tert-butyl ester as yellow solid. MS: $(M+H)^+$ 570.4. 3-Benzyl-7-(4-tert-butoxycarbonyl-piperazin-1-yl)-2-methanesulfonyl-indole-1-carboxylic acid tert-butyl ester was then dissolved in dichloromethane and treated with trifluoroacetic acid to give 3-benzyl-2-methanesulfonyl-7-piperazin-1-yl-1H-indole as a TFA salt, MS: $(M+H)^+$ 370.

Example 7

3-Benzyl-7-piperazin-1-yl-1H-indole-2-carboxylic Acid Amide

The synthetic procedures described in this Example were carried out according to the process shown in Scheme I.

SCHEME I

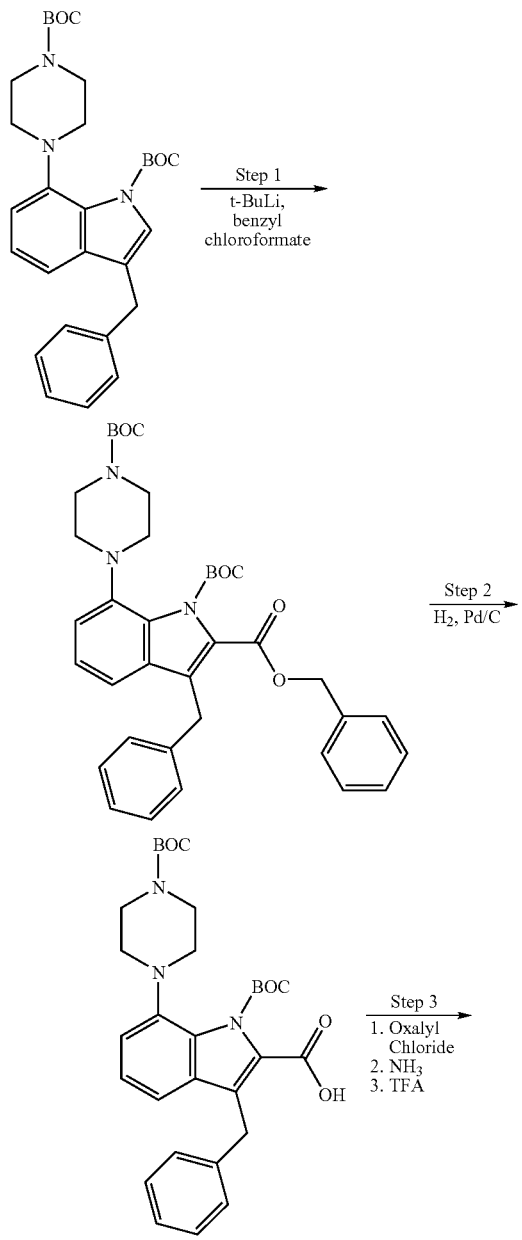

Step 1 3-Benzyl-7-(4-tert-butoxycarbonyl-piperazin-1-yl)-indole-1,2-dicarboxylic acid 2-benzyl ester 1-tert-butyl ester A solution of 3-benzyl-7-(4-tert-butoxycarbonyl-piperazin-1-yl)-indole-1-carboxylic acid tert-butyl ester (200 mg, 0.41 mmol) in THF (10 ml) was cooled to −78° C., and t-BuLi (1 ml, 1.7 M in pentane) was added. After stirring at −78° C. for 20 minutes, 0.15 ml of benzyl chloroformate was added and the reaction was allowed to warm up to room temperature for 30 minutes. Water was slowly added, followed by EtOAc. The organic layer was separated and washed with water and brine. After drying over MgSO$_4$, the organic fraction was concentrated in vacuo and the resulting residue was purified by flash chromatography to give 3-benzyl-7-(4-tert-butoxycarbonyl-piperazin-1-yl)-indole-1,2-dicarboxylic acid 2-benzyl ester 1-tert-butyl ester as a yellow solid (100 mg, 39%). MS: (M+H)$^+$ 626.4.

Step 2 3-Benzyl-7-(4-tert-butoxycarbonyl-piperazin-1-yl)-indole-1,2-dicarboxylic acid 1-tert-butyl ester 3-Benzyl-7-(4-tert-butoxycarbonyl-piperazin-1-yl)-indole-1,2-dicarboxylic acid 2-benzyl ester 1-tert-butyl ester (100 mg, 0.16 mmol) in EtOH (20 ml) was added to a Parr vessel containing catalytic amount of 5% Pd on carbon. The vessel was purged with 2.76 Bar of hydrogen After shaking for one hour, the reaction mixture was filtered through Celite and concentrated under reduced pressure to give 3-benzyl-7-(4-tert-butoxycarbonyl-piperazin-1-yl)-indole-1,2-dicarboxylic acid 1-tert-butyl ester (72 mg, 84%). MS: (M+H)$^+$ 536.4.

Step 3
3-Benzyl-7-piperazin-1-yl-1H-indole-2-carboxylic acid amide

3-Benzyl-7-piperazin-1-yl-1H-indole-2-carboxylic acid amide was prepared using the procedure of step 4 of Example 1, followed by treatment with trifluoroacetic acid to yield the TFA salt. MS: (M+H)$^+$ 335.

Example 8

3-Benzyl-5-methyl-7-piperazin-1-yl-benzofuran-2-carboxylic Acid Amide

The synthetic procedures described in this Example were carried out according to the process shown in Scheme J.

SCHEME J

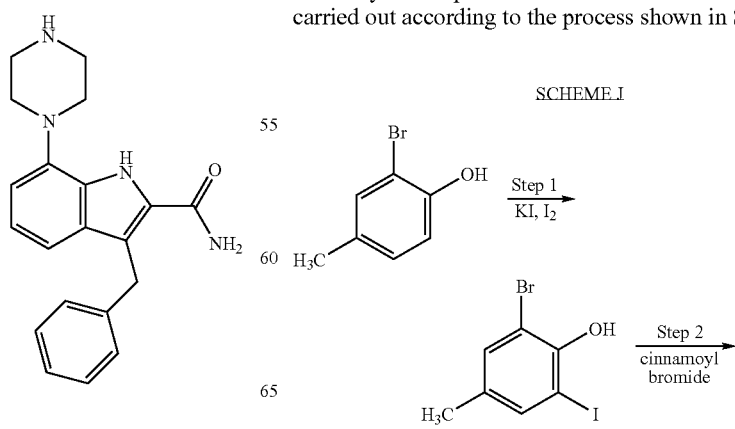

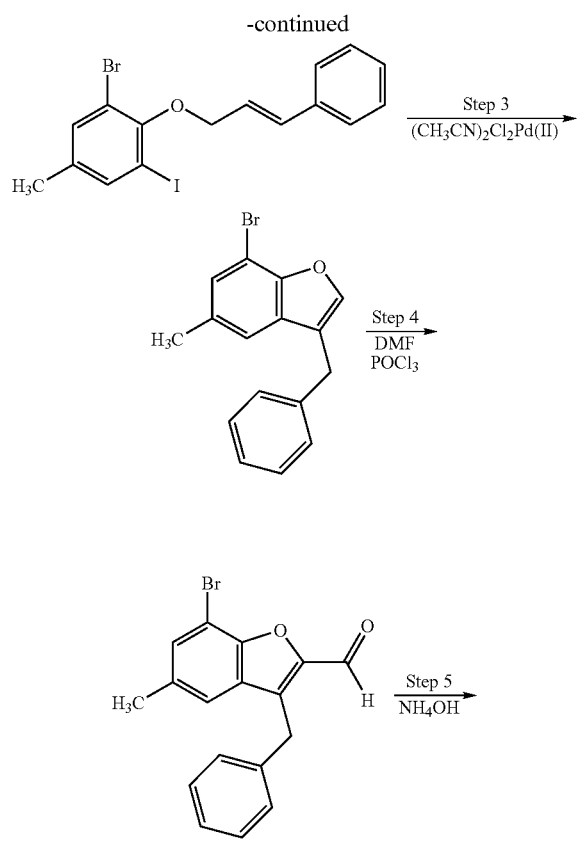

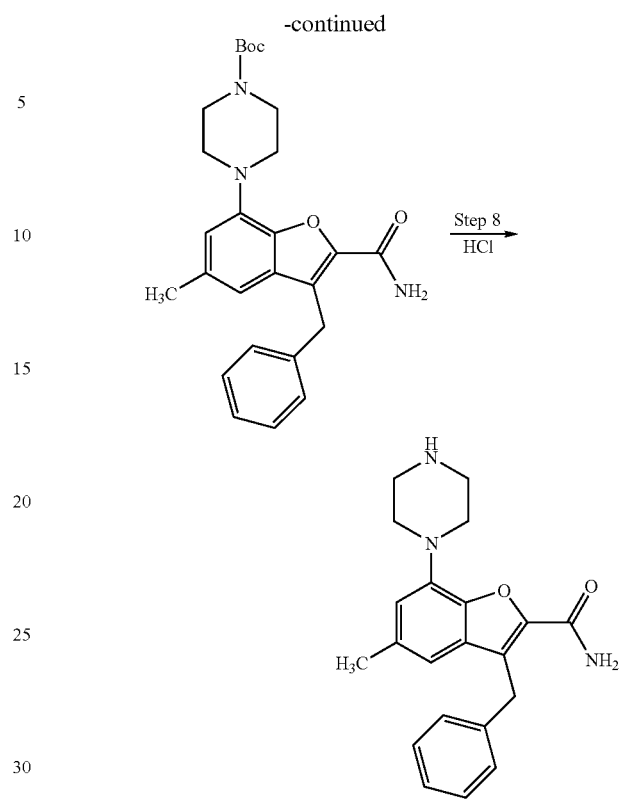

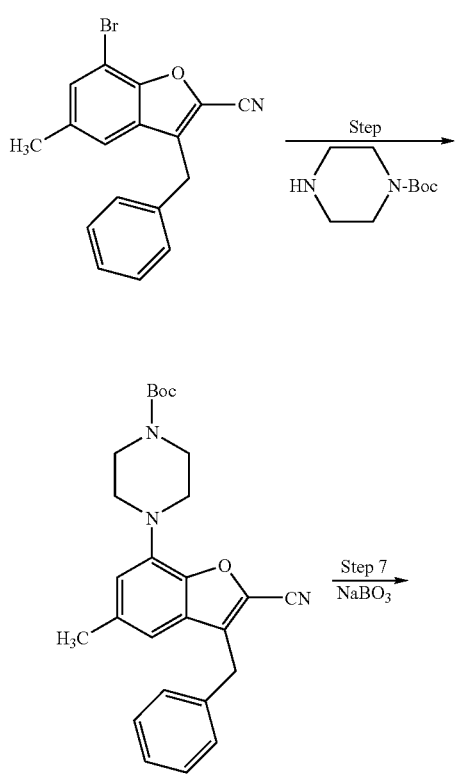

Step 1 2-Bromo-4-methyl-6-iodophenol

2-Bromo-4-methylphenol (10.11 gm, 54.05 mmol) was mixed with concentrated ammonium hydroxide (50 ml) and methanol (20 ml). Potassium iodide (17.94 g, 108 mmol), iodine (13.72 g, 54.05 mmol) and water (60 ml) were mixed to give a dark brown solution which was added in portions to the phenol solution. Additional methanol (200 ml) was added in portions as precipitating product made the mixture too viscous to stir. When all the iodine solution had been added the mixture was heated to 60° C. till the brown color faded. The mixture was cooled, filtered and the solid rinsed three times with water. The solid was dissolved in dichloromethane, dried over magnesium sulfate, filtered and stripped to give 2-Bromo-4-methyl-6-iodophenol as an oil that crystallized on standing. The filtrate and water rinses were concentrated and extracted twice with ethyl acetate, dried over magnesium sulfate, filtered and stripped to give additional 2-bromo-4-methyl-6-iodophenol for a total of 16.24 g, 96% yield.

Step 2 1-Bromo-3-iodo-5-methyl-2-(3-phenylallyloxy)-benzene

2-Bromo-4-methyl-6-iodophenol (7.82 gm, 25 mmol) and cinnamyl bromide (4.93 g, 25 mmol) were added to DMF (20 ml). Diisopropylethylamine (5.3 ml, 30.4 mmol) was added and the mixture heated to 60° C. for 15 minutes and then allowed stir for 16 hours at room temperature. The DMF was removed under vacuum, and 1M HCl was added until the residue was acidic. The mixture was extracted with ethyl acetate, and the combined organic phase was dried over magnesium sulfate, filtered, and concentrated under reduced pressure to give 1-bromo-3-iodo-5-methyl-2-(3-phenylallyloxy)-benzene (10.86 g, 100% yield).

Step 3 3-Benzyl-7-bromo-5-methyl-benzofuran

1-Bromo-3-iodo-5-methyl-2-(3-phenylallyloxy)-benzene (10.86 g, 25 mmol), tetrabutylammonium chloride (7.65 gm, 27.5 mmol), sodium carbonate (6.62 g, 62.46 mmol), sodium formate (1.7 g, 25 mmol), and bis(acetonitrile)dichloropalladium(II) (0.467 g, 1.8 mmol) was added to 50 ml DMF. The mixture was degassed and heated under nitrogen at 80° C. for 105 minutes, then cooled to room temperature. Water was added and the mixture was extracted with a hexanes/ethyl acetate (1:1) mixture. The solution was dried onto 20 gm silica gel, the silica gel was layered over 100 gm silica gel in a fritted funnel and eluted with four 400 ml portions of hexanes. The hexanes was removed under reduced pressure to give 3-benzyl-7-bromo-5-methyl-benzofuran (3.97 g, 52% yield). MS: (M+H)$^+$ 302.

Step 4 3-Benzyl-7-bromo-5-methyl-benzofuran-2-carbaldehyde

3-Benzyl-7-bromo-5-methyl-benzofuran (3.93 g, 13.05 mmol) was mixed with 10 ml DMF. Phosphorus oxychloride (1.8 ml, 19.3 mmol) was added and the reaction mixture was heated to 50° C. for 16 hours. Additional phosphorus oxychloride (3.6 ml, 38.6 mmol) was added and the reaction mixture was heated to 90° C. for an hour, then to 100° C. for five hours. The mixture was cooled to room temperature, poured onto ice and aqueous sodium hydroxide was added until the mixture reached pH=3. The mixture was extracted with ethyl acetate, dried over magnesium sulfate, filtered, and absorbed onto 20 gm silica gel. The silica gel was layered over 100 gm silica gel in a fritted funnel and eluted with five portions of 400 ml hexanes (to give 0.33 g recovered starting material) and two portions of 400 ml of 10/90 ethyl acetate/hexane to give 3-benzyl-7-bromo-5-methyl-benzofuran-2-carbaldehyde (2.61 g, 61% yield). MS: (M+H)$^+$ 330.

Step 5 3-Benzyl-7-bromo-5-methyl-benzofuran-2-carbonitrile

3-Benzyl-7-bromo-5-methyl-benzofuran-2-carbaldehyde (2.61 gm, 7.93 mmol) was added to a mixture of THF (10 ml) and concentrated ammonium hydroxide (80 ml). Iodine (2.2 g, 8.67 mmol) was added and the grey slurry was stirred overnight. Additional THF (20 ml), ammonium hydroxide (20 ml), and iodine (0.2 g, 0.8 mmol) were added, and the mixture stirred for 30 minutes. The reaction mixture was quenched by addition of aqueous 10% sodium thiosulfate (20 ml) and brine (20 ml). The mixture was extracted with diethy ether, and the combined organic phase was dried over magnesium sulfate, filtered and concentrated under reduced pressure to give 3-benzyl-7-bromo-5-methyl-benzofuran-2-carbonitrile (2.5 g, 97% yield). (M+H)$^+$ 327.

Step 6 4-(3-Benzyl-2-cyano-5-methyl-benzofuran-7-yl)-piperazine-1-carboxylic acid tert-butyl ester In an oven dried flask was added BINAP (racemic, 0.17 g, 0.913 mmol), cesium carbonate (0.35 g, 1.07 mmol), tris(dibenzylideneacetone)dipalladium (0.0207 g, 0.0226 mmol), 1-BOC-piperazine (0.17 g, 0.913 mmol) and 5 ml DMF. The flask was evacuated and refilled with nitrogen. 3-benzyl-7-bromo-5-methyl-benzofuran-2-carbonitrile (0.29 g, 0.90 mmol) in 5 ml DMF was added via syringe and the mixture heated to 80° C. overnight, then to 100° C. for another 24 hours. The mixture was concentrated on a rotary evaporator and purified by column chromatography (1:9 ethyl acetate/hexane) to give 4-(3-benzyl-2-cyano-5-methyl-benzofuran-7-yl)-piperazine-1-carboxylic acid tert-butyl ester (0.174 g, 45% yield) as a yellow solid.

Step 7 4-(3-Benzyl-2-carbamoyl-5-methyl-benzofuran-7-yl)-piperazine-1-carboxylic acid tert-butyl ester 4-(3-Benzyl-2-cyano-5-methyl-benzofuran-7-yl)-piperazine-1-carboxylic acid tert-butyl ester (0.302 gm, 0.7 mmol), sodium perborate tetrahydrate (0.43 gm, 2.8 mmol), ethanol (8 ml) and water (8 ml) were combined in a vial and heated in a microwave reactor to 130° C. for 10 minutes. The reaction mixture was cooled to room temperature, diluted with brine and water and extracted three times with ethyl acetate. The solution was dried over magnesium sulfate and purified by column chromatography (methanol/dichloromethane gradient) to give 4-(3-benzyl-2-carbamoyl-5-methyl-benzofuran-7-yl)-piperazine-1-carboxylic acid tert-butyl ester (0.25 gm, 80% yield).

Step 8 3-Benzyl-5-methyl-7-piperazin-1-yl-benzofuran-2-carboxylic acid amide 4-(3-Benzyl-2-carbamoyl-5-methyl-benzofuran-7-yl)-piperazine-1-carboxylic acid tert-butyl ester was deprotected using ethanolic HCl, following the procedure of step 4 of Example 2, to provide 3-benzyl-5-methyl-7-piperazin-1-yl-benzofuran-2-carboxylic acid amide as a hydrochloride salt, (M+H)$^+$ 350.

Example 9

3-Benzyl-5-methyl-7-piperazin-1-yl-benzofuran-2-carboxylic Acid methylamide and 3-Benzyl-5-methyl-7-piperazin-1-yl-benzofuran-2-carboxylic Acid dimethylamide The synthetic procedures described in this Example were carried out according to the process shown in Scheme K.

SCHEME K

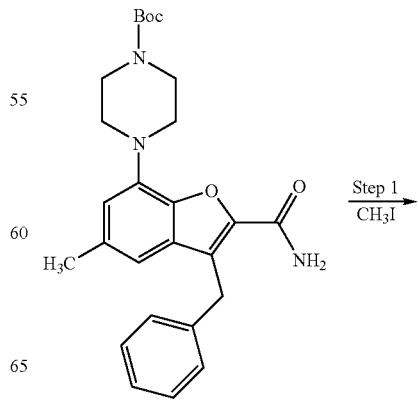

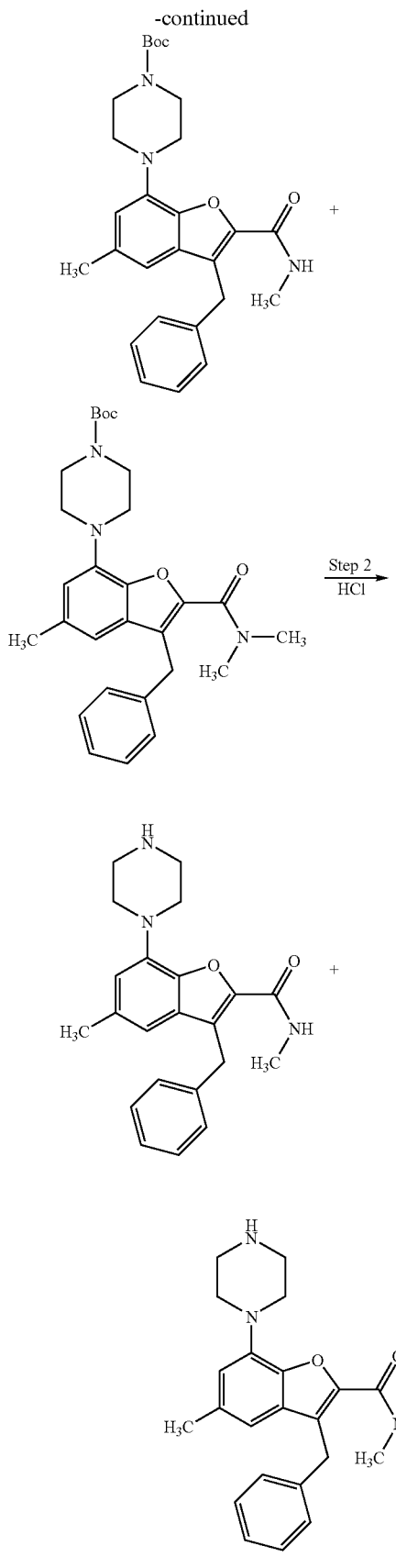

Step 1 4-(3-Benzyl-5-methyl-2-methylcarbamoyl-benzofuran-7-yl)-piperazine-1-carboxylic acid methyl ester and 4-(3-Benzyl-2-dimethylcarbamoyl-5-methyl-benzofuran-7-yl)-piperazine-1-carboxylic acid isopropyl ester 4-(3-Benzyl-2-carbamoyl-5-methyl-benzofuran-7-yl)-piperazine-1-carboxylic acid tert-butyl ester (0.25 gm, 0.556 mmol) was dissolved in 5 ml DMF and sodium hydride (60% in oil, 0.033 gm, 0.83 mmol) was added, resulting in formation of a precipitate. Methyl iodide (0.052 ml, 0.83 mmol) was added and the solid dissolved to give a clear solution. After one hour the mixture was concentrated under reduced pressure and the residue was purified by preparative thin layer chromatography (3/97 methanol/dichloromethane). One band was again purified (40/60, tetrahydrofuran/hexane) to give 4-(3-Benzyl-5-methyl-2-methylcarbamoyl-benzofuran-7-yl)-piperazine-1-carboxylic acid tert-butyl ester. A second band was recrystallized from acetonitrile to give 4-(3-Benzyl-2-dimethylcarbamoyl-5-methyl-benzofuran-7-yl)-piperazine-1-carboxylic acid tert-butyl ester.

Step 2 3-Benzyl-5-methyl-7-piperazin-1-yl-benzofuran-2-carboxylic acid methylamide and 3-Benzyl-5-methyl-7-piperazin-1-yl-benzofuran-2-carboxylic acid dimethylamide 4-(3-Benzyl-5-methyl-2-methylcarbamoyl-benzofuran-7-yl)-piperazine-1-carboxylic acid methyl ester and 4-(3-Benzyl-2-dimethylcarbamoyl-5-methyl-benzofuran-7-yl)-piperazine-1-carboxylic acid isopropyl ester were each separately treated with ethanolic HCl, following the procedure of step 4 of Example 2, to provide 3-benzyl-5-methyl-7-piperazin-1-yl-benzofuran-2-carboxylic acid methylamide ((M+H)$^+$ 364) and 3-benzyl-5-methyl-7-piperazin-1-yl-benzofuran-2-carboxylic acid dimethylamide ((M+H)$^+$ 378) respectively.

Example 10

3-Benzyl-5-methyl-7-piperidin-4-yl-benzofuran-2-carboxylic Acid Amide

The synthetic procedures described in this Example were carried out according to the process shown in Scheme L.

SCHEME L

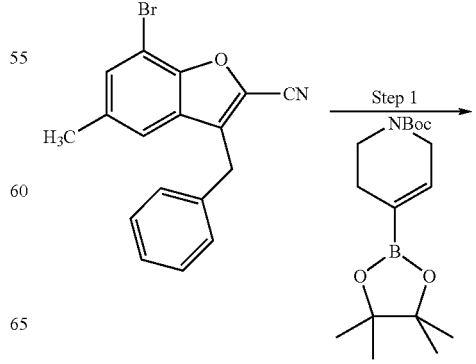

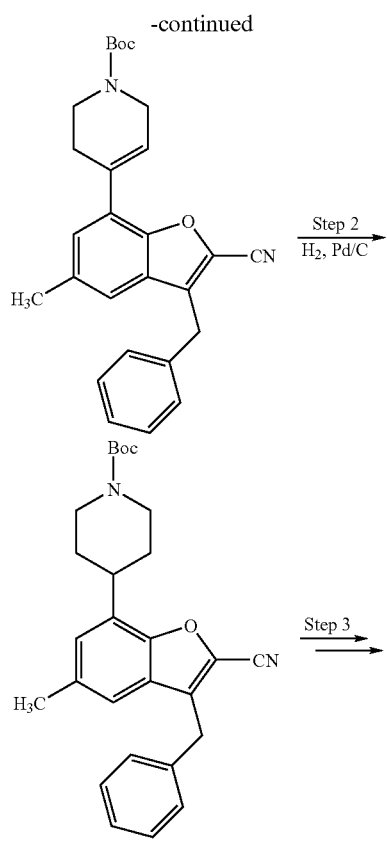

boxylic acid tert-butyl ester as a residue that was used directly in the next step without further characterization.

Step 2 4-(3-Benzyl-2-cyano-5-methyl-benzofuran-7-yl)-piperidine-1-carboxylic acid tert-butyl ester The crude 4-(3-benzyl-2-cyano-5-methyl-benzofuran-7-yl)-3,6-dihydro-2H-pyridine-1-carboxylic acid tert-butyl ester from step 1 was dissolved in ethanol, and 10% palladium on carbon was added. The mixture was shaken under hydrogen (2.76 Bar) for 40 hours. After filtering off the catalyst, the mixture was concentrated under reduced pressure and purified using preparative thin layer chromatography (1/9 ethyl acetate/hexanes) to give 4-(3-benzyl-2-cyano-5-methyl-benzofuran-7-yl)-piperidine-1-carboxylic acid tert-butyl ester.

Step 3 3-Benzyl-5-methyl-7-piperidin-4-yl-benzofuran-2-carboxylic acid amide

Following the procedure of steps 7 and 8 of Example 8, 4-(3-benzyl-2-cyano-5-methyl-benzofuran-7-yl)-piperidine-1-carboxylic acid tert-butyl ester was converted to 3-benzyl-5-methyl-7-piperidin-4-yl-benzofuran-2-carboxylic acid amide, $(M+H)^+$ 349.

Example 11

1-[5-Fluoro-3-(3-fluoro-benzyl)-2-methanesulfonyl-benzofuran-7-yl]-piperazine

The synthetic procedures described in this Example were carried out according to the process shown in Scheme M.

SCHEME M

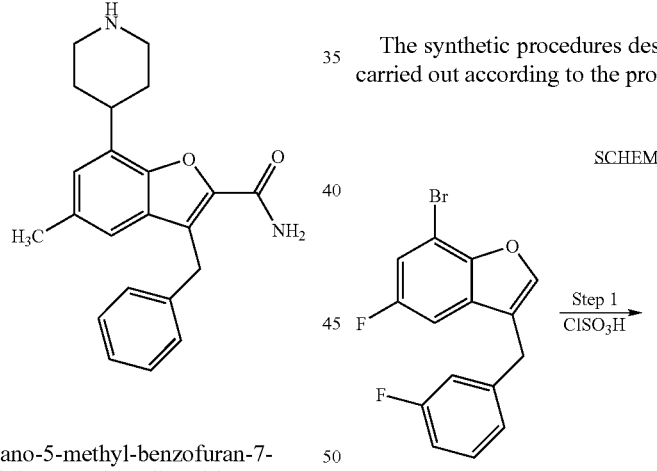

Step 1 4-(3-Benzyl-2-cyano-5-methyl-benzofuran-7-yl)-3,6-dihydro-2H-pyridine-1-carboxylic acid tert-butyl ester To a flask was added 3-benzyl-7-bromo-5-methyl-benzofuran-2-carbonitrile (0.13 gm, 0.40 mmol), 4-(4,4,5,5-Tetramethyl-[1,3,2]dioxaborolan-2-yl)-3,6-dihydro-2H-pyridine-1-carboxylic acid tert-butyl ester (0.161 gm, 0.52 mmol), [1,1'-bis(diphenylphosphino) ferrocene]dichloropalladium (0.020 gm, 0.0245 mmol), and potassium carbonate (0.124 gm, 0.9 mmol). Dimethylfomamide was added via syringe and the mixture evacuated and refilled with nitrogen, then heated for 16 hours at 80° C. The mixture was concentrated under vacuum, water was added, and the mixture was extracted with ethyl acetate. The combined organic phase was dried over magnesium sulfate, filtered, and concentrated under reduced pressure to give crude 4-(3-benzyl-2-cyano-5-methyl-benzofuran-7-yl)-3,6-dihydro-2H-pyridine-1-car-

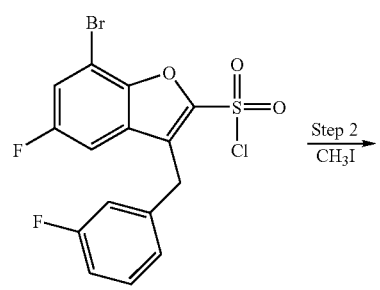

-continued

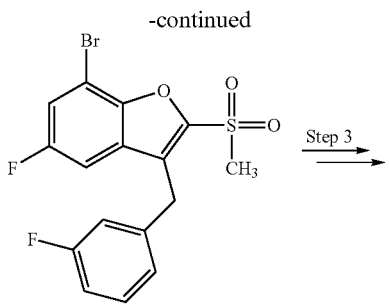

Step 1

7-Bromo-5-fluoro-3-(3-fluoro-benzyl)-benzofuran (0.97 gm, 3.0 mmol, prepared from 2-bromo-4-fluoro-phenol and 3-fluoro-cinnamaldehyde following the procedure of steps 1 and 2 of Example 8) was dissolved in dichloromethane (30 ml) and chilled to −15° C. Chlorosulfonic acid (0.26 ml, 3.9 mmol) in dichloromethane (2 ml) was added in portions, and the reaction mixture was stirred for 10 minutes then warmed to room temperature and stirred for 16 hours. To the resulting slurry was added pyridine (0.33 ml, 4.08 mmol) and phosphorus pentachloride (0.812 gm, 3.9 mmol) and the reaction mixture was stirred for 24 hours. Water was added and the reaction mixture was stirred for 30 minutes. The organic layer was separated, dried over magnesium sulfate, dried onto silica gel, and layered over a pad of silica gel in a fritted funnel. The silica gel was eluted with ethyl acetate/hexanes (1/9) to give 7-bromo-5-fluoro-3-(3-fluoro-benzyl)-benzofuran-2-sulfonyl chloride.

Step 2 7-Bromo-5-fluoro-3-(3-fluoro-benzyl)-2-methanesulfonyl-benzofuran

7-Bromo-5-fluoro-3-(3-fluoro-benzyl)-benzofuran-2-sulfonyl chloride (0.63 gm, 1.5 mmol) was dissolved in THF (5 ml) and added dropwise to a mixture of sodium sulfite (0.504 gm, 4 mmol) and sodium bicarbonate (0.336 gm, 4 mmol) in water (12 ml). The mixture was refluxed for three hours, cooled to room temperature, and methyl iodide (0.75 ml, 12 mmol) was added. The mixture was heated to 50° C. for two hours then cooled to room temperature and stirred for 16 hours. The mixture was diluted with water and extracted twice with dichloromethane. The solution was dried over magnesium sulfate and purified by preparative thin layer chromatography (1/4, ethyl acetate/hexanes) to give 7-bromo-5-fluoro-3-(3-fluoro-benzyl)-2-methanesulfonyl-benzofuran (0.35 gm, 58% yield), (M+H)+ 402.

Step 3 1-[5-Fluoro-3-(3-fluoro-benzyl)-2-methanesulfonyl-benzofuran-7-yl]-piperazine 1-[5-Fluoro-3-(3-fluoro-benzyl)-2-methanesulfonyl-benzofuran-7-yl]-piperazine was prepared from 7-bromo-5-fluoro-3-(3-fluoro-benzyl)-2-methanesulfonyl-benzofuran following the procedure of steps 6 and 8 of Example 8, (M+H)+ 407.

Example 12

1-[5-Fluoro-3-(3-fluoro-benzyl)-7-piperazin-1-yl-benzofuran-2-yl]-ethanone

The synthetic procedures described in this Example were carried out according to the process shown in Scheme N.

SCHEME N

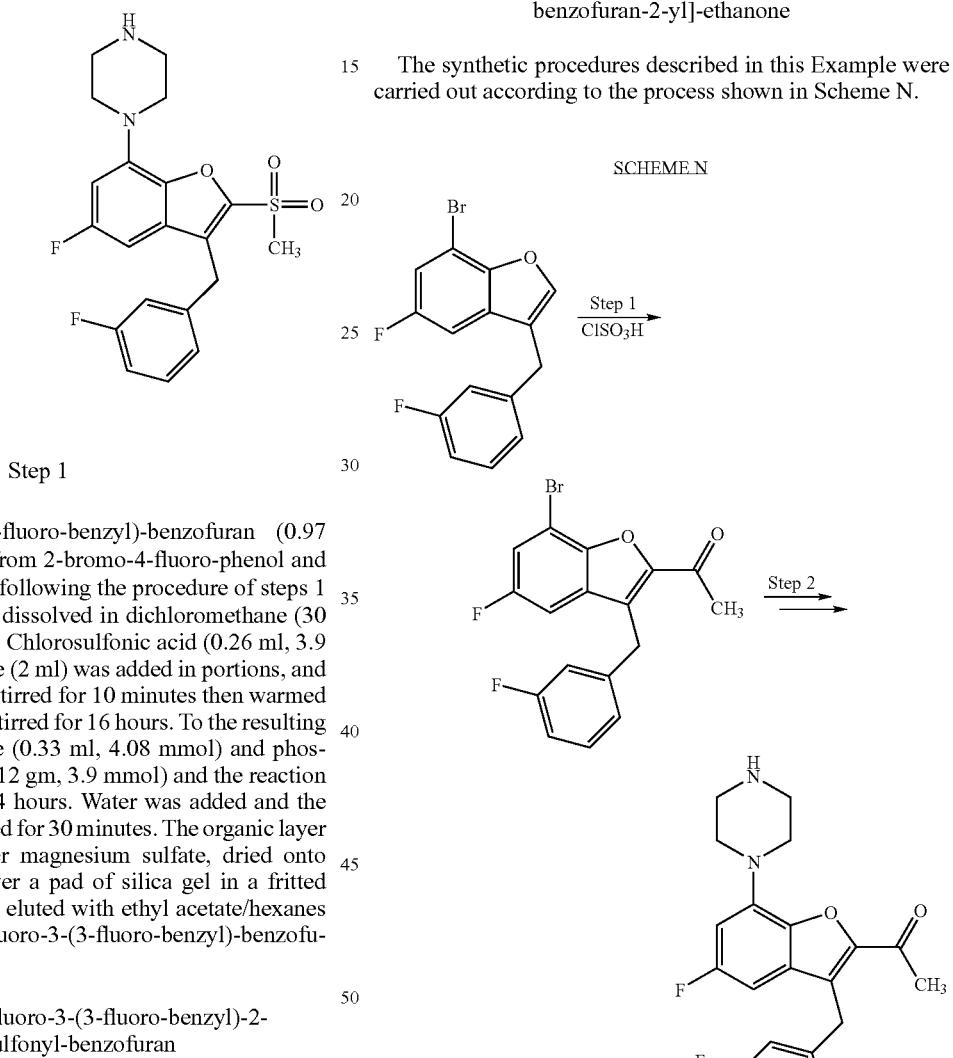

Step 1 1-[7-Bromo-5-fluoro-3-(3-fluoro-benzyl)-benzofuran-2-yl]-ethanone

7-Bromo-5-fluoro-3-(3-fluoro-benzyl)-benzofuran (1.29 gm, 4 mmol), acetyl chloride (0.57 ml, 8 mmol) and dichloromethane (16 ml) were added to an oven dried flask and chilled in ice bath. Aluminum chloride (1.067 gm, 8 mmol) was added and after 5 minutes the reddish brown mixture was allowed to warm to room temperature and stir overnight. The mixture was diluted with hydrochloric acid (0.1M) and extracted three times with dichloromethane. The extracts were dried over magnesium sulfate and purified by column chromatography (ethyl acetate/hexane gradient) to give 1-[7-Bromo-5-fluoro-3-(3-fluoro-benzyl)-benzofuran-2-yl]-ethanone (1.2 gm, 82% yield).

Step 2 1-[5-Fluoro-3-(3-fluoro-benzyl)-7-piperazin-1-yl-benzofuran-2-yl]-ethanone 1-[7-Bromo-5-fluoro-3-(3-fluoro-benzyl)-benzofuran-2-yl]-ethanone was converted to 1-[5-fluoro-3-(3-fluoro-benzyl)-7-piperazin-1-yl-benzofuran-2-yl]-ethanone following the procedure of steps 6 and 8 of Example 8, (M+H)+ 407.

Example 13

1-[5-Fluoro-3-(3-fluoro-benzyl)-7-pyrrolidin-3-yl-benzofuran-2-yl]-ethanone

The synthetic procedures described in this Example were carried out according to the process shown in Scheme O.

SCHEME O

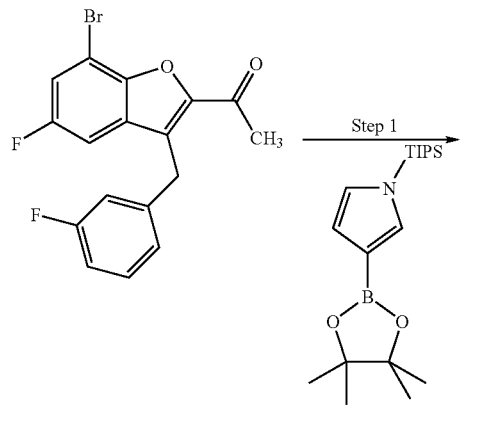

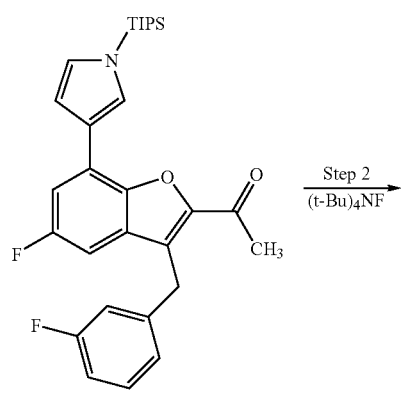

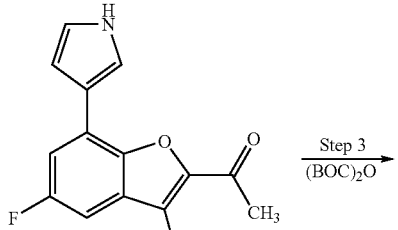

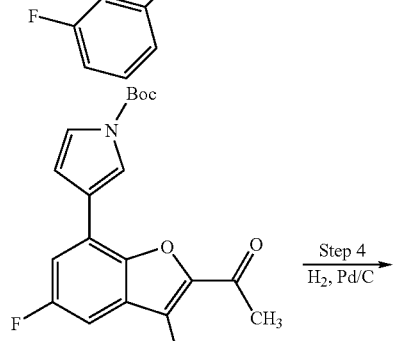

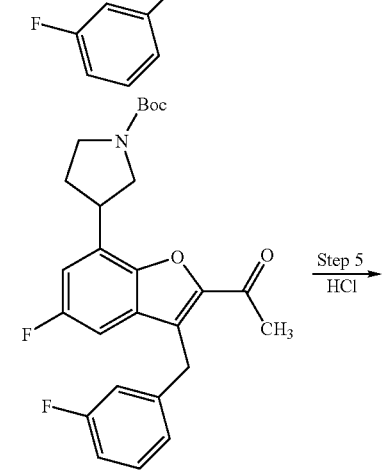

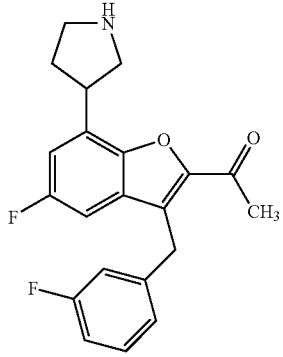

Step 1 1-[5-Fluoro-3-(3-fluoro-benzyl)-7-(1-triisopropylsilanyl-1H-pyrrol-3-yl)-benzofuran-2-yl]-ethanone To a flask was added 7-bromo-5-fluoro-3-(3-fluoro-benzyl)-benzofuran (0.365 gm, 1.0 mmol), [1,1'-bis(diphenylphosphino)ferrocene]dichloropalladium (0.010 gm, 0.012 mmol), potassium phosphate (0.425 gm, 2.0 mmol), 1-(triisopropylsilyl)pyrrole-3-boronic acid (0.365 gm, 1.37 mmol), DME (12 ml) and water (2 ml). The mixture was evacuated and refilled with nitrogen while being sonicated. The mixture was heated in a microwave reactor for 15 minutes at 70° C., then for 15 minutes at 100° C., and then for 15 minutes at 130° C. The mixture was cooled, concentrated under reduced pressure, diluted with brine and extracted with ethyl acetate. The organic phase was absorbed onto a pad of silica gel that was rinsed with ethyl acetate/hexanes (250 ml, 1/9) and eluted to give 1-[5-fluoro-3-(3-fluoro-benzyl)-7-(1-triisopropylsilanyl-1H-pyrrol-3-yl)-benzofuran-2-yl]-ethanone (0.38 gm, 75% yield).

Step 2 1-[5-Fluoro-3-(3-fluoro-benzyl)-7-(1H-pyrrol-3-yl)-benzofuran-2-yl]-ethanone 1-[5-Fluoro-3-(3-fluoro-benzyl)-7-(1-triisopropylsilanyl-1H-pyrrol-3-yl)-benzofuran-2-yl]-ethanone (0.38 gm, 0.748 mmol) and tetrabutylammonium fluoride hydrate (0.28 gm, 0.89 mmol) were added to tetrahydrofuran (10 ml) and stirred at room temperature for four hours. The solution was concentrated under reduced pressure and purified by column chromatography to give 1-[5-fluoro-3-(3-fluoro-benzyl)-7-(1H-pyrrol-3-yl)-benzofuran-2-yl]-ethanone (0.205 gm, 79% yield).

Step 3 3-[2-acetyl-5-fluoro-3-(3-fluoro-benzyl)-benzofuran-7-yl]-pyrrole-1-carboxylic acid tert-butyl ester 1-[5-Fluoro-3-(3-fluoro-benzyl)-7-(1H-pyrrol-3-yl)-benzofuran-2-yl]-ethanone (0.205 gm, 0.58 mmol), di-t-butyl dicarbonate (0.153 gm, 0.70 mmol), and DMAP (0.0232 gm, 0.18 mmol) were dissolved in acetonitrile and stirred at room temperature for 16 hours. The acetonitrile was removed under vacuum and potassium phosphate monobasic solution (0.2M) was added, and the mixture extracted with ethyl acetate. The combined organic phase was dried over magnesium sulfate and solvent was removed under vacuum to give 3-[2-acetyl-5-fluoro-3-(3-fluoro-benzyl)-benzofuran-7-yl]-pyrrole-1-carboxylic acid tert-butyl ester (0.26 gm, 100% yield).

Step 4 3-[2-Acetyl-5-fluoro-3-(3-fluoro-benzyl)-benzofuran-7-yl]-pyrrolidine-1-carboxylic acid tert-butyl ester 3-[2-Acetyl-5-fluoro-3-(3-fluoro-benzyl)-benzofuran-7-yl]-pyrrole-1-carboxylic acid tert-butyl ester (0.114 gm, 0.253 mmol) and platinum (5% on carbon, 0.035 gm) were added to ethyl alcohol (45 ml) and placed under hydrogen (balloon) at 55° C. for two hours. Additional platinum (5% on carbon, 0.065 gm) was added and heated at 60° C. under hydrogen for three hours. The mixture was filtered, concentrated and purified by column chromatography (ethyl acetate/hexane gradient) to give 3-[2-acetyl-5-fluoro-3-(3-fluoro-benzyl)-benzofuran-7-yl]-pyrrolidine-1-carboxylic acid tert-butyl ester (0.096 gm, 83% yield).

Step 5 1-[5-Fluoro-3-(3-fluoro-benzyl)-7-pyrrolidin-3-yl-benzofuran-2-yl]-ethanone 1-[5-Fluoro-3-(3-fluoro-benzyl)-7-pyrrolidin-3-yl-benzofuran-2-yl]-ethanone was prepared by treating 3-[2-acetyl-5-fluoro-3-(3-fluoro-benzyl)-benzofuran-7-yl]-pyrrolidine-1-carboxylic acid tert-butyl ester with ethanolic HCl using the procedure described for step 4 of Example 2, $(M+H)^+$ 356.

Example 14

3-Fluoro-1-(4-fluoro-benzyl)-4-piperazin-1-yl-1H-indole-2-carboxylic Acid Amide

The synthetic procedures described in this Example were carried out according to the process shown in Scheme P.

SCHEME P

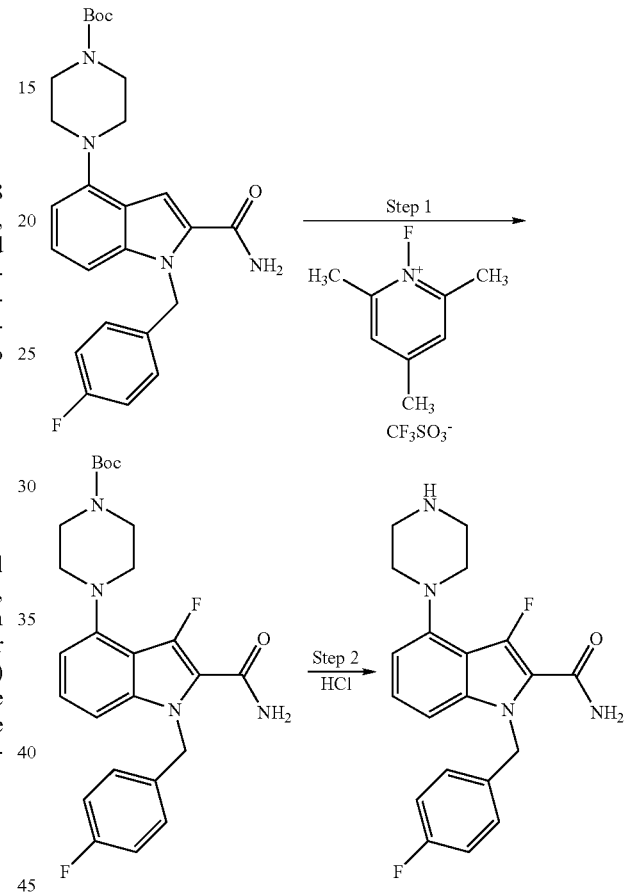

Step 1 4-[2-carbamoyl-3-fluoro-1-(4-fluoro-benzyl)-1H-indol-4-yl]-piperazine-1-carboxylic acid tert-butyl ester 4-[2-Carbamoyl-1-(4-fluoro-benzyl)-1H-indol-4-yl]-piperazine-1-carboxylic acid tert-butyl ester (0.0155 gm, 0.034 mmol) was dissolved in dichloromethane and 1-fluoro-2,4,6-trimethylpyridinium triflate (85%, 0.012 gm, 0.035 mmol) was added and the reaction mixture was stirred at room temperature overnight. The mixture was transferred onto two preparative thin layer chromatography plates and eluted with 1/1 ethyl acetate/hexane, then further purified on two analytical thin layer chromatography plates (1/1 ethyl acetate/hexane), and then additionally purified on two more analytical plates (35/65 ethyl acetate/hexane) to give 4-[2-carbamoyl-3-fluoro-1-(4-fluoro-benzyl)-1H-indol-4-yl]-piperazine-1-carboxylic acid tert-butyl ester (0.009 gm, 56% yield).

Step 2 3-Fluoro-1-(4-fluoro-benzyl)-4-piperazin-1-yl-1H-indole-2-carboxylic acid amide 3-Fluoro-1-(4-fluoro-benzyl)-1H-indol-4-yl]-piperazine-1-carboxylic acid tert-butyl ester was deprotected with ethanolic HCl to afford 3-Fluoro-1-(4-fluoro-benzyl)-4-piperazin-1-yl-1H-indole-2-carboxylic acid amide, following the procedure described for step 4 of Example 2, (M+H)+ 371.

Example 15

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 16

Radioligand Binding Studies

This example illustrates in vitro radioligand binding studies of compound of formula I.

The binding activity of compounds of this invention in vitro was determined as follows. Duplicate determinations of 5-HT$_6$ ligand affinity were made by competing for binding of [$^3$H]LSD in cell membranes derived from HEK293 cells stably expressing recombinant human 5-HT$_6$ receptor. Duplicate determinations of 5-HT$_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K$_i$ cells stably expressing recombinant human 5-HT$_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June; 115(4):622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT$_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[\text{ligand}] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be 5-HT6 and/or 5-HT2A antagonists. For example, 1-(3-fluoro-benzyl)-4-piperazin-1-yl-1H-indole-2-carboxylic acid methylamide exhibited a pKi of approximately 9.90 for the 5-HT6 receptor, and 3-(3-fluoro-benzyl)-5-methyl-7-piperazin-1-yl-benzofuran-2-carboxylic acid amide exhibited a pKi of approximately 8.91 for the 5-HT2A receptor.

Example 17

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for enhancing cognitive memory in an Alzheimer's patient, said method comprising administering to said Alzheimer's patient a therapeutically effective amount of a compound of formula III:

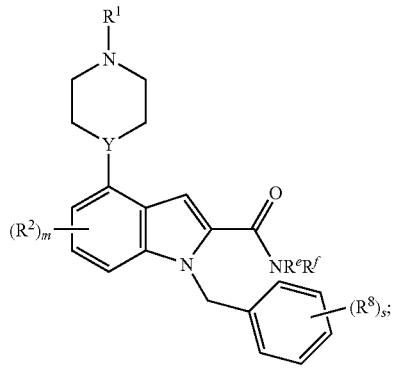

wherein:
 s is 0 or 1;
 m is 0 or 1;
 Y is N;
 R$^1$ is hydrogen or methyl;
 R$^2$ is halo or C$_{1-6}$alkyl;
 R$^8$ is halo, C$_{1-6}$alkyl, halo-C$_{1-6}$alkoxy, C$_{1-6}$alkoxy or cyano; and
 R$^e$ and R$^f$ each independently is hydrogen or methyl.

2. The method of claim 1, wherein R$^1$ is hydrogen.
3. The method of claim 1, wherein R$^2$ is halo.
4. The method of claim 1, wherein R$^8$ is halo.
5. The method of claim 1, wherein R$^e$ and R$^f$ are hydrogen.

* * * * *